United States Patent
Wang

(10) Patent No.: US 9,777,259 B2
(45) Date of Patent: Oct. 3, 2017

(54) SOMATIC STEM CELLS

(71) Applicant: StemBios Technologies, Inc., Monterey Park, CA (US)

(72) Inventor: James Wang, Monterey Park, CA (US)

(73) Assignee: StemBios Technologies, Inc., Monterey Park, CA (US)

( * ) Notice: Subject to any disclaimer, the term of this patent is extended or adjusted under 35 U.S.C. 154(b) by 191 days.

(21) Appl. No.: 14/877,585

(22) Filed: Oct. 7, 2015

(65) Prior Publication Data

US 2016/0024468 A1 Jan. 28, 2016

Related U.S. Application Data

(62) Division of application No. 13/629,884, filed on Sep. 28, 2012.

(60) Provisional application No. 61/540,191, filed on Sep. 28, 2011, provisional application No. 61/609,522, filed on Mar. 12, 2012.

(51) Int. Cl.
```
C12N 5/071      (2010.01)
A61M 1/36       (2006.01)
A61K 35/545     (2015.01)
C12N 5/074      (2010.01)
A61F 2/02       (2006.01)
```

(52) U.S. Cl.
CPC ............ C12N 5/067 (2013.01); A61K 35/545 (2013.01); A61M 1/36 (2013.01); C12N 5/0607 (2013.01); A61F 2/022 (2013.01); C12N 2501/04 (2013.01); C12N 2501/11 (2013.01); C12N 2501/115 (2013.01); C12N 2501/12 (2013.01); C12N 2501/125 (2013.01); C12N 2501/135 (2013.01); C12N 2501/155 (2013.01); C12N 2501/16 (2013.01); C12N 2501/22 (2013.01); C12N 2501/237 (2013.01); C12N 2501/415 (2013.01)

(58) Field of Classification Search
None
See application file for complete search history.

(56) References Cited

U.S. PATENT DOCUMENTS

| | | |
|---|---|---|
| 6,004,807 A | 12/1999 | Banchereau et al. |
| 6,440,735 B1 | 8/2002 | Gaeta |
| 6,716,422 B1 | 4/2004 | Gajewski et al. |
| 6,916,654 B1 | 7/2005 | Sims et al. |
| 6,986,887 B2 | 1/2006 | Lawman et al. |
| 7,316,932 B2 | 1/2008 | Woodside |
| 7,575,921 B2 | 8/2009 | Vacanti et al. |
| 7,651,690 B2 | 1/2010 | Jensen et al. |
| 7,972,847 B2 | 7/2011 | Kalinski |
| 8,158,758 B2 | 4/2012 | Gurney |
| 8,206,907 B2 | 6/2012 | Milstein et al. |
| 8,337,858 B2 | 12/2012 | Scoglio et al. |
| 8,394,630 B2 | 3/2013 | Wang et al. |
| 8,673,296 B2 | 3/2014 | Karlsson-Parra et al. |
| 2002/0115059 A1 | 8/2002 | Terada et al. |
| 2003/0161817 A1 | 8/2003 | Young et al. |
| 2004/0136967 A1 | 7/2004 | Weiss et al. |
| 2004/0175823 A1 | 9/2004 | Vacanti et al. |
| 2005/0255588 A1 | 11/2005 | Young et al. |
| 2006/0035373 A1 | 2/2006 | Zhang et al. |
| 2006/0040392 A1 | 2/2006 | Collins et al. |
| 2006/0171931 A1 | 8/2006 | Rudnicki et al. |
| 2006/0252150 A1 | 11/2006 | Cheng et al. |
| 2007/0190023 A1 | 8/2007 | Battista et al. |
| 2008/0152665 A1 | 6/2008 | Leclerc et al. |
| 2008/0305079 A1 | 12/2008 | Chen et al. |
| 2009/0004661 A1 | 1/2009 | Shetty |
| 2009/0104158 A1 | 4/2009 | Young et al. |
| 2009/0104160 A1 | 4/2009 | Young et al. |
| 2009/0155225 A1 | 6/2009 | Ratajczak et al. |
| 2009/0186334 A1 | 7/2009 | Young et al. |
| 2010/0081199 A1 | 4/2010 | Slukvin et al. |
| 2010/0183570 A1 | 7/2010 | Wang et al. |
| 2011/0305673 A1 | 12/2011 | Spees |
| 2012/0021482 A1 | 1/2012 | Zuba-Surma et al. |
| 2012/0028355 A1 | 2/2012 | Sato et al. |
| 2012/0034194 A1 | 2/2012 | Wang |
| 2012/0177670 A1 | 7/2012 | Wang |
| 2013/0095077 A1 | 4/2013 | Wang |

(Continued)

FOREIGN PATENT DOCUMENTS

| | | |
|---|---|---|
| CN | 102008650 | 4/2011 |
| EP | 1632563 | 3/2006 |

(Continued)

OTHER PUBLICATIONS

Aiuti, et al., "Expression of CXCR4, the Receptor for Stromal Cell-derived Factor-1 on Fetal and Adult Human Lympho-hematopoietic Progenitors", European Journal of Immunology. Published 1999. Wiley-VCH Verlag GmbH, Weinheim. pp. 1823-1831.

Aoyama et al. "Stromal cell CD9 regulates differentiation of hematopoietic stem/progenitor cells" Hematopoiesis, Blood, 93(8):2586-2594, 1999.

Banerjee et al. "An antibody to the tetraspan membrane protein CD9 promotes neurite formation in a partially α3β1 integrin-dependent manner" The Journal of Neuroscience 17(8):2756-2765, 1997.

Barker, et al., "Identification of stem cells in small intestine and colon by marker gene Lgr5", Articles, Nature Publishing Group, Oct. 2007.

Barker, et al., "Lgr5+ve Stem Cells Drive Self-Renewal in the Stomach and Build Long-Lived Gastric Units In Vitro", Cell Stem Cell, vol. 6, Jan. 2010.

(Continued)

Primary Examiner — Scott Long
Assistant Examiner — Nghi Nguyen
(74) Attorney, Agent, or Firm — Cesari and McKenna, LLP

(57) ABSTRACT

A somatic stem cell that is CD10+, CXCR4+, and CD31+ and another somatic stem cell that is CD105+, CD44+, and nestin+. Also disclosed are both a method of preparing these stem cells and a method of using them to treat degenerative diseases, e.g., a muscle-degenerative disease. The invention further includes making and using liver cells derived from the somatic cell that is CD105+, CD44+, and nestin+.

7 Claims, 4 Drawing Sheets

(56) References Cited

U.S. PATENT DOCUMENTS

| | | |
|---|---|---|
| 2013/0189327 A1 | 7/2013 | Ortega et al. |
| 2013/0236485 A1 | 9/2013 | Wang |
| 2014/0161774 A1 | 6/2014 | Wang |
| 2014/0219952 A1 | 8/2014 | Cameron |
| 2014/0377760 A1 | 12/2014 | Wang et al. |
| 2016/0166611 A1 | 6/2016 | Wang |

FOREIGN PATENT DOCUMENTS

| | | |
|---|---|---|
| EP | 2818544 A1 | 12/2014 |
| JP | H0391491 | 4/1991 |
| JP | 2001-128660 | 5/2001 |
| WO | WO-99/26639 | 6/1999 |
| WO | WO-2006/028723 | 3/2006 |
| WO | WO-2006/070370 | 7/2006 |
| WO | WO-2007/026353 | 3/2007 |
| WO | WO-2007/087367 | 8/2007 |
| WO | WO-2008/148105 | 12/2008 |
| WO | WO-2009/012357 | 1/2009 |
| WO | WO-2009/059032 | 5/2009 |
| WO | WO-2009/061024 | 5/2009 |
| WO | WO-2009/136283 | 11/2009 |
| WO | WO-2010/039241 | 4/2010 |
| WO | WO-2010/083203 | 7/2010 |
| WO | WO-2010/099044 | 9/2010 |
| WO | WO-2011/137540 | 11/2011 |
| WO | WO-2012/019002 | 2/2012 |
| WO | WO-2013/049459 | 4/2013 |

OTHER PUBLICATIONS

Battula, et al. "Prospective isolation and characterization of mesenchymal stem cells from human placenta using a frizzled-9-specific monoclonal antibody", Differentiation, 2008, vol. 76, pp. 326-336.

Battula, et al., "Human placenta and bone marrow derived MSC cultured in serum-free, b-FGF-containing medium express cell surface frizzled-9 and SSEA-4 and give rise to multilinelage differentiation", Differentiation, Spinger Verlag, DE, col. 75, No. 4, Apr. 2007.

Bellato, et al., Pain Research and Treatment vol. 2012 pp. 1-7.

Buhring et al. "Novel markers for the prospective isolation of human MSC" Ann. N.Y. Acad. Sci. 1106:262-271, 2007.

Cai, et al., (NeuroMolecular Medicine, 2002, vol. 2, pp. 233-249).

Cui et al. "Spatial distribution and initial changes of SSEA-1 and other cell adhesion-related molecules on mouse embryonic stem cells before and during differentiation" Journal of Histochemistry & Cytochemistry, 52(11):1447-1457, 2004.

Fickert et al. "Identification of subpopulations with characteristics of mesenchymal progenitor cells from human osteoarthritic cartilage using triple staining for cell surface markers" Arthritis Research & Therapy, 6(5):R422-R432, 2004.

Furusawa et al. "Embryonic stem cells expressing both platelet endothelial cell adhesion molecule-1 and stage-specific embryonic antigen-1 differentiate predominantly into epiblast cells in a chimeric embryo" Biology of Reproduction, 70:1452-1457 (2004).

Gang et al. Prospective isolation of MSC with SSEA-4; Blood First Edition Paper, prepublished on line Oct. 24, 2006: DOI 10.1182/blood-2005-11-010504.

Gang et al. "SSEA-4 identifies mesenchymal stem cells from bone marrow", Stem Cells in Hematology, Blood, 109(4):1743-1751, 2007.

Glazar et al. "IgSF8 (EWI-2) and CD9 in fertilization: Evidence of distinct functions for CD9 and a CD9-associated protein in mammalian sperm-egg interaction" Reprod Fertil Dev. 21(2):293-303, 2009.

Huang et al. "Isolation and characterization of cell subpopulation with stem cell properties in human and monkey intervertebral disc (IVD)" EMC Journal 2009 p. 28.

Hung, et al., "Isolation and characterization of size-sieved stem cells from human bone marrow", Stem Cells, Alphamed Press, vol. 20, No. 3, 2002.

Hur, "Highly Angiogenic CXCR4 and CD31 monocyte subset derived from 3D culture of human peripheral blood", Biomaterials, 2013, pp. 1929-1941.

Jaks, et al, "Lgr5 marks cycling, yet long-lived, hair follicle stem cells," Nature Genetics, vol. 40, No. 11, 1291-1299 (2008).

Kadam et al. "Islet neogenesis from the constitutively nestin expressing human umbilical cord matrix derived mesenchmal stem cells" Islets 2:2, 112-120, 2010.

Kim et al. "Role of CD9 in proliferation and proangiogenic action of human adipose-derived mesenchymal stem cells" Cell and Molecular Physiology Eur. J. Physiol 455:283-296, 2007.

Kim, et al., "Generation of human induced pluripotent stem cells from osteoarthritis patient-derived synovial cells", Arthritis and Rheumatism, 6(10):3010-2021 (2011).

Kogler, et al., "A new human somatic stem cell from placental cord blood with intrinsic pluripotent differentiation potential", Journal of Experimental Medicine, vol. 200, No. 2, 2004.

Kucia et al. "Evidence that very small embryonic like (VSEL) stem cells are mobilized into peripheral blood" Stem Cells Express, published online Jun. 5, 2008; doi:10.1634/stemcells.2007-0922 p. 1-23.

Kucia, et al., "A population of very small embryonic-like (VSEL) CXCR4+SSEA=1+Oct4+ stem cells identified in adult bone marrow", Leukemia, vol. 20, 2006.

Kucia, et al., "Morphological and molecular characterization of novel population of CXCR4+ SSEA=4+ very small embryonic-like cell purified from human cord blood-preliminary report", Leukemia, vol. 21, 2007.

Kucia, et al., "Physiological and pathological consequences of identification of very small embryonic like (VSEL) stem cells in adult bone marrow", Journal of Physiology and Pharmacology, 2006, 57, Supp 5, 5-18.

Lian et al. "Establishing clonal cell lines with endothelial-like potential from CD9hi, SSEA-1 Cells in embryonic stem cell-derived embryoid bodies" PLoS ONE 1:(e6)1-10, 2006.

Lindvall, et al., J. Clin Invest. Jan. 4, 2010; 120(1): 29-40.

Magnus, et al., Philos Trans R Soc Lond B Biol Sci. Jan. 12, 2008; 363 (1489): 9-22.

Meng et al. "Endometrial regenerative cells: A novel stem cell population" Journal of Translational Medicine, 5:(57)1-10, 2007.

Meregalli, et al., BioDrugs 2010, vol. 24, Issue 4, pp. 237-247.

Muller et al. "A novel embryonic stem cell like derived from the common marmoset monkey (Callithrix jacchus) exhibiting germ cell-like characteristics" Human Reproduction, 24(6):1359-1372, 2009.

Negroni, et al., Expert Opin Biol Ter. Feb. 2011; 11(2):157-176.

Noggle, et al., "Notch signaling is inactive but inducible in human embryonic stem cells", Stem Cells, vol. 24, No. 7, 2006.

Oka et al. "CD9 is associated with leukemia inhibitory factor-mediated maintenance of embryonic stem cells" Molecular Biology of the Cell, 13:1274-1281, 2002.

Promise et al. "Multiplexed staining of live human embryonic stem cells for flow cytometric analysis of pluripotency markers" Stem Cells and Development, 18(8): 1135-1139, 2009.

Ratajczak, et al., "Very small embryonic-like (VSEL) stem cells: purification from adult organs, characterization, and biological significance", Stem Cell Reviews, vol. 4, No. 2, 2008.

Sackstein, et al., "Ex vivo glycan engineering on cd44 programs human multipotent mesenchymal stromal cell trafficking to bone", Nat. Med., vol. 14, pp. 181-187, 2008.

Sato, et al., "Paneth cells constitute the niche for Lgr5 stem cells in intestinal crypts", Nature, vol. 469, Jan. 2011.

Shinohara et al. "CD9 is a surface marker on mouse and rat male germline stem cells", Biology of Reproduction, 70:70-75, 2004.

Shmilovici "Mammalian spore-like cells—A reservoir of spare parts for old-age?" Medical Hypotheses, 2007, 68:767-769.

Stout et al. "Primitive stem cells residing in the skeletal muscle of adult pigs are mobilized into the peripheral blood after trauma" The American Surgeon, 73:1106-1110, 2007.

Tole et al. "Distribution of CD9 in the developing and mature rat nervous system" Developmental dynamics 197:94-106, 1993.

Tourandre, et al., Arthritis & Rheumatism vol. 64, No. 2, pp. 533-541, 2012.

(56) References Cited

OTHER PUBLICATIONS

Trubiani et al. "Expression profile of the embryonic markers nanog. OCT-4, SSEA-1, SSEA-4, and frizzled-9 receptor in human periodontal ligament mesenchymal stem cells" 2010 DOI.10.1002/jcp. 22203p. 1-14.

Vacanti et al. "Identification and initial characterization of spore-like cells in adult mammals" Journal of Cellular Biochemistry, 80:455-460, 2001.

Wojakowski et al "Very Small Embryonic-Like Stem Cells in Cardiovascular Repair" Pharmacology & Therapeutics vol. 129, pp. 21-28. 2011.

Young "Existence of Reserve quiescent stem cells in adults, from amphibians to humans" Immunol., 280:71-109, 2004.

Young et al. "Cancer gene mechanisms and gene therapy" Reviews, Minerva Biotec. 17:55-63, 2005.

Yu, et al., Liver Transpl. Jan. 2012; 18 (1): 9-21.

Zuba-Surma, et al., "'Small stem cells' in adult tissues: Very small embryonic-like stem cells stand up!", Cytometry Part A, vol. 75A, No. 1, 2009.

Zulewski et al. "Multipotential nestin-positive stem cells isolated from adult pancreatic islets differentiate ex vivo into pancreatic endocrine, exocrine, and hepatic phenotypes" Diabetes, 50:521-533, 2001.

http://stemcells.nih.gov/info/glossary.asp.

Abeyta, et al., 2004, Human Molecular Genetics, vol. 13, No. 6, pp. 601-608.

Allergrucci, et al., 2006, Human Reproduction Update, vol. Advance Access published on Aug. 26, 2006, p. 1-18.

Amit, et al., "Feeder Layer-and Serum-Free Culture of Human Embryonic Stem Cells", Biology of Reproduction, 2004, vol. 70, pp. 837-845.

Arechaga et al.; "Characterisation of new intracellular membranes in Escherichia coli accompanying large scale over-production of the b subunit of F1F0 ATP synthase"; FEBS Letters 482:215-219 (2000).

Bizzetto et al.; "Outcomes after related and unrelated umbilical cord blood transplantation for hereditary bone marrow failure syndromes other than fanconi anemia"; Haematologica 96(1)134-141 (2011).

Dolcetti, et al., "Myeloid-Derived Suppressor Cell Rolse in Tumor-Related Inflammation", Cancer Letters; 267:216-225 (2008).

Fitton, et al., "Therepaies from Fucoidan; Multifunction Marine Polymers", Marine Drugs, vol. 9, No. 12, Dec. 30, 2011, pp. 1731-1760.

Gabrilovich, et al., "Myeloid-Derived-Suppressor Cells as Regulators of the Immune System", Nat. Rev. Immunol.; 9(3):162-176 (2009).

Hamman, et al. 2005, Biodrugs, vol. 19, No. 3, pp. 165-177.

Haraguchi, et al., "CD13 is a therapeutic target in human liver cancer stem cells", Jornal of Clinical Investigation, vol. 120, No. 9, Sep. 1, 2010, pp. 3326-3339.

Irhimeh, et al., "Fucoidan ingestion increases the expression of CXCR4 on human CD34 +cells", Experimental Hematology, vol. 35, No. 6, Jun. 1, 2007, pp. 989-994.

Jensen, et al., "Mobilization of human CD34<+>CD133<+> and CD34<+>CD133<-> stem cells in vivo by consumption of an extract from Aphanizomenon flos-aquae-related to modulation of CXCR4 expression by an L-selectin ligand?", Cardiovascular Revascularization Medicine, Elsevier, NL, vol. 8, No. 3, Aug. 29, 2007 pp. 189-202.

Li, et al., 2009, Transplant Immunology, vol. 21, pp. 70-74.

Lv, et al., "Concise Review: The Surface Markers and Identity of Human Mesenchymal Stem Cells", Stem Cells vol. 32, pp. 1408-1419, 2014.

Ostrand-Rosenberg, et al., "Myeloid-Derived Suppressor Cells: Linking Inflammation and Cancer", J. Immunol.; 182:4499-4506 (2009).

Sato, et al., 2003, Developmental Biology, vol. 260 p. 404-413.

Schuldiner, et al., "Effects of eight growth factors on the differentiation of cells derived from human embryonic stem cells", PNAS, 2000, vol. 97, pp. 11307-11312.

Serafini, et al., "Myeloid Suppressor Cells in Cancer: Recruitment, Phenotype, Properties, and Mechanisms of Immune Suppression", Seminars in Cancer Biology; 16:53-65 (2006).

Sharp III, et al., 2014, Frontiers in Oncology, vol. 4, Article 299, p. 1-13.

Sinha et al.; "Prostaglandin E2 promotes tumor progression by inducing myeloid-derived suppressor cells"; Cancer Res, 67(9):4507-4513 (2007).

Sprangers, et al., 2008, Kidney Immunology, vol. 74, pp. 14-21.

Stemrx Bio Science, "Get Rid of Ankylosing Spondylitis with Stem Cell Treatment and Applied Therapies", 2013.

Sweeney, et al., "Mobilization of stem/progenitor cells by sulfated polysaccharides does not require selectin presence", Proceedings of the National Academy of Sciences, National Academy of Sciences, U.S., vol. 97, No. 12, Jun. 6, 2000 pp. 6544-6549.

Taha, 2010, Current Stem Cell Research & Therapy, vol. 5, pp. 23-36.

Talmadge, "Pathways Mediating the Expansion and Immunosuppressive Activity of Myeloid-Derived Suppressor Cells and Their Relevance to Cancer Therapy", Clin. Cancer Res.; 13918:5243-5248 (2007).

Tennis, et al. Neoplasia 2012; 12:244-53.

Tu et al.; "Overexpression of interleukin-1 beta induces gastric inflammation and cancer and mobilizes myeloid-derived suppressor cells in mice"; Cancer Cell, 14(5):408-419 (2008).

Wang, et al., "Effects and Safety of Allogenic Mecenchymal Stem Cell Intravenous Infusion in Active Ankylosing Spondylitis Patients Who Failed NSAIDs: A 20-Week Clinical Trial", Cell Transplantation, vol. 23, pp. 1293-1303, 2013.

Wu, et al., 2012, Ageing Research Reveiws, vol. 11, pp. 32-40.

Young et al.: "Adult-derived stem cells and their potential for use in tissue repair and molecular medicine"; J. Cell. Mol. Med., 9(3):753-769 (2005).

Zhao, et al. "A human peripheral blood monocyt-derived subset acts as pluripotent stem cells", Proceedings of the National Academy of Sciences, National Academy of Sciences, vol. 100, No. 5, pp. 2426-2431, Mar. 4, 2003.

Karaoz, et al., "Characterization of mesenchymal stem cells from rat bone marrow: ultrastructural properties, differentiation potential and immunophenotypic markers", Histochem Cell Biol (2009) 132:533-546.

Phadnis, et al., "Mesenchyman Stem Cells Derived from Bone Marrow of Diabetic Patients Portrait Unique Markers Influenced by the Diabetic Microenvironment", The Review of Diabetic Studies, vol. 6, No. 4, 2009, pp. 260-270.

Zhao, et al., "Embryonic Stem Cell Markers", Molecules, 2012, 17, 6196-6236.

Hsu, et al., "Characterization of Two LGR Genes Homologous to Gonadotropin and Thyrotopin Receptors with Extracellular Leucine-Rich Repeats and a G Protein-Coupled, Seven-Transmembrane Region", Mol. Endocrinology, 1998, vol. 12, No. 12, pp. 1830-1845).

Ratajczak, et al., "Bone Marrow—Home of Versatile Stem Cells", Transfuion Medicine and Hemotherapy 2008;35:248-259.

Choi, "Adult Stem Cell Therapy for Autoimmune Disease", International Journal of Stem Cells vol. 2, No. 2, 2009.

SOMATIC STEM CELLS

CROSS-REFERENCE TO RELATED APPLICATIONS

This application is a division of U.S. application Ser. No. 13/629,884, filed on Sep. 28, 2012, which claims priority to U.S. Provisional Application No. 61/540,191, filed on Sep. 28, 2011, and also to U.S. Provisional Application No. 61/609,522, filed on Mar. 12, 2012. The contents of all prior applications are hereby incorporated by reference herein in their entirety.

BACKGROUND

Stem cells are totipotent, pluripotent, or multipotent cells that can differentiate in vivo or in vitro into many or all cell types. Due to their pluripotency, embryonic stem (ES) cells are believed to hold great potential for treating degenerative or inherited diseases. Yet, ethical considerations have hampered the use of human ES cells. Stem cells of a non-embryonic origin would circumvent this obstacle. Thus, there is a need for non-embryonic stem cells.

SUMMARY

This invention relates to somatic stem cells and related methods.

One aspect of this invention relates to an isolated somatic non-adherent stem cell that is CD10+, CXCR4+, and CD31+. This cell is named "SB-3 cell" herein. The sign "+" following a cell marker stands for a higher fluorescent staining with a marker-specific antibody, as compared to a lower fluorescent staining with an isotype control of the antibody. The sign "−" following a cell marker stands for the same fluorescent staining with a marker-specific antibody as that with an isotype control of the antibody.

Another aspect of this invention relates to an isolated somatic adherent stem cell that is CD105+, CD44+, and nestin+. This cell is named "SB-4 cell" herein.

In still another aspect, the invention features a cell bank including a plurality of populations of somatic stem cells. The somatic stem cells are each CD10+, CXCR4+, and CD31+, and the populations are originated from different subjects. The subjects can be humans or non-humans.

In yet another aspect, the invention features a cell bank including a plurality of populations of somatic stem cells. The somatic stem cells are each CD105+, CD44+, and nestin+, and the populations are originated from different subjects. The subjects can be humans or non-humans.

Within the scope of this invention as well is a method for treating a muscle injury or a muscle-degenerative disease. The method includes administering to a subject in need thereof an effective amount of the somatic stem cells that are CD10+, CXCR4+, and CD31+. Examples of the muscle-degenerative disease include muscular dystrophy, fibromyalgia, myopathies, dermatomyositis, polymyositis, rhabdomyolysis, and myocarditis.

The invention further features another method for treating a muscle injury or a muscle-degenerative disease. The method includes administering to a subject in need thereof an effective amount of the somatic stem cells that are CD105+, CD44+, and nestin+.

Also contemplated herein is a method of preparing somatic stem cells. The method includes (1) obtaining from a subject (e.g., a human or non-human) a bodily fluid sample (e.g., blood, bone marrow, umbilical cord blood, menstrual fluid, and amniotic fluid) containing a plurality of cells, (2) incubating the sample with a divalent cation chelating agent (e.g., EDTA, EGTA, and sodium citrate) or heparin in a container until the sample is separated into an upper layer and a lower layer, (3) collecting the upper layer, (4) isolating from the upper layer a population of somatic stem cells that are 0.3-6.0 micrometers in size, and (5) culturing the isolated somatic stem cells in a medium containing specific growth factors: R-Spondin-1, SCF, G-CSF, bFGF, EGF, and PDGF. Somatic stem cells can be positive for CD10, CXCR4, and CD31. They can also be positive for CD105, CD44, and nestin.

Further contemplated is a method of preparing liver cells from the above-described somatic stem cells that are CD105+, CD44+, and nestin+. The method includes culturing the isolated somatic stem cells in a first differentiating medium containing activin; culturing the isolated somatic stem cells in a second differentiating medium containing basic fibroblast growth factors (bFGF) and bone morphogenetic protein 2 (BMP2); further culturing the isolated somatic stem cells in a third differentiating medium containing hepatocyte growth factor (HGF), dexamethasone (DEX), and oncostatin M (OSM); and collecting liver cells thus obtained, the liver cells expressing albumin, transferrin, and hepatocyte nuclear factor 3B (HNF3B).

The invention also includes an extracorporeal bioartificial liver device. The device has a cartridge that contains an array of hollow fibers and the liver cells prepared in the manner described above. The liver cells express one or more proteins selected from the group consisting of albumin, alpha-1-antitrypsin, factor V, complement C3, antithrombin III, and transferrin. They are placed in the extracapillary space between the hollow fibers, which are each formed of a membrane having a pore size of about 0.1 μm to 0.3 μm. The cartridge can have a cylindrical shape with a first opening on the side wall close to one terminus and a second opening also on the side wall but close to the other terminus. The first opening is affixed to a first passage and the second opening is affixed to a second passage, the two passages each extending away from the cartridge.

In addition, the invention features a method of treating acute liver failure. The method includes identifying a subject in need of treatment, attaching the above-described extracorporeal bioartificial liver device to an artery of the subject through the first passage and a vein of the subject through the second passage, perfusing blood from the subject through the capillary space inside each of the hollow fibers in the cartridge, and allowing cleansing of blood by permitting the crossover of toxic solutes from the blood to the liver cells cultured in the extracapillary space between the hollow fibers and also allowing the diffusion of vital metabolites from the liver cells to the blood returning to the subject. The subject can be a human who suffers from a chronic liver disease, which most commonly results from hepatitis C infection, alcohol abuse, and drug overdose. In an embodiment, the subject is awaiting liver transplantation.

Also described herein is a method of producing albumin. The method includes culturing in a medium liver cells prepared using the method described above, and collecting from the medium albumin produced by the liver cells.

The details of one or more embodiments of the invention are set forth in the accompanying drawings and the description below. Other features, objects, and advantages of the invention will be apparent from the description and drawing, and from the claims.

DETAILED DESCRIPTION

Figure 1:
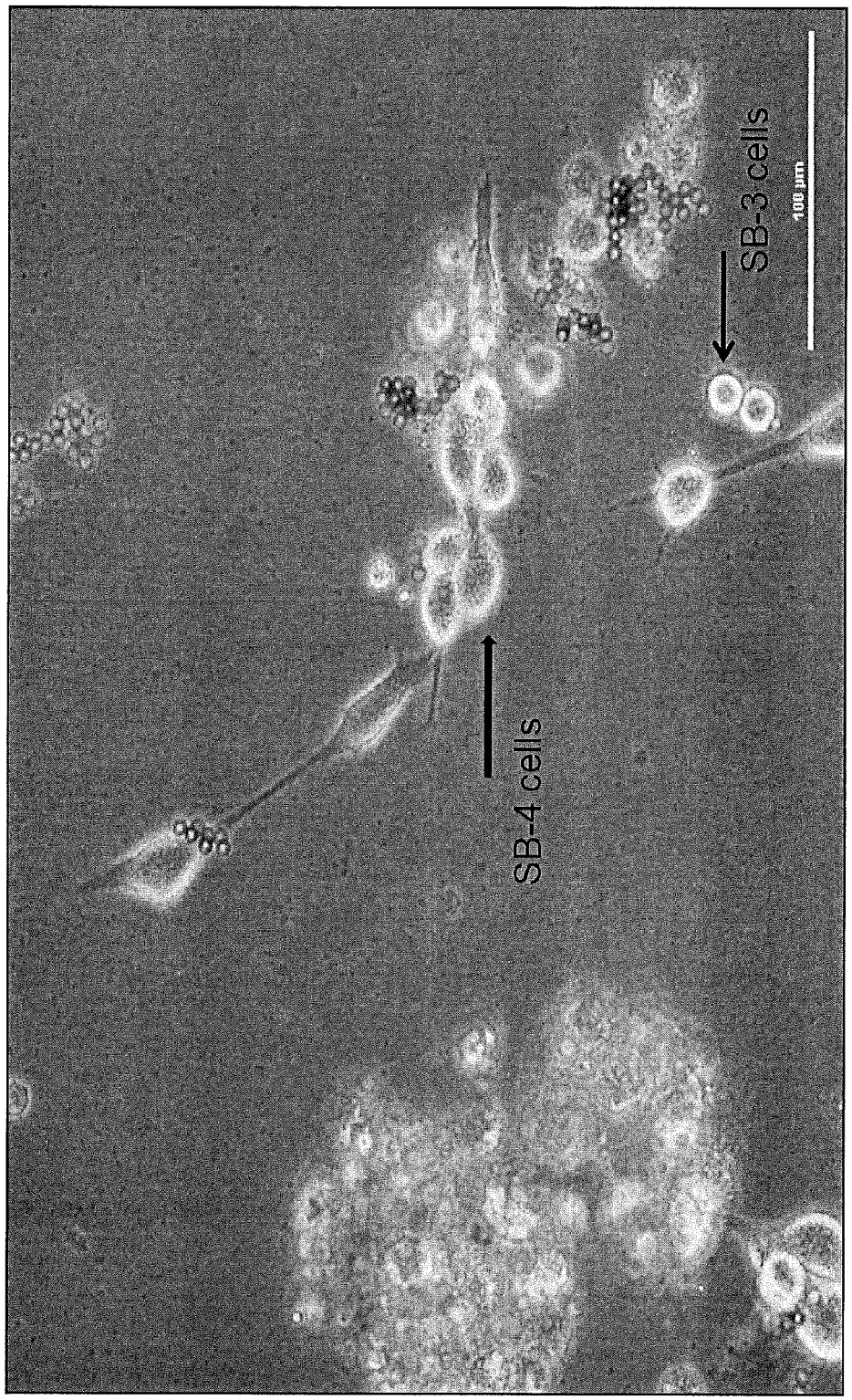
FIG. 1 is a photograph showing SB-3 cells and SB-4 cells in a culture.

This invention is based, at least in part, on the unexpected discoveries that (i) non-adherent cells that are positive for CD10, CXCR4, and CD31 (i.e., SB-3 cell) can be differentiated into three germ layers; and (ii) that these cells can become adherent cells that are positive for CD105, CD44, and nestin (i.e., SB-4 cell).

SB-3 Cells and SB-4 Cells

SB-3 and SB-4 cells can be prepared from a cell population that is isolated from a bodily fluid sample (e.g., blood, bone marrow, umbilical cord blood, menstrual fluid, and amniotic fluid). The bodily fluid sample can be obtained from a human or from a non-human. Examples of a non-human, from which the above-mentioned somatic stem cells can be obtained, include, but are not limited to primate, dog, rodent, guinea pigs, cat, horse, cow, sheep, and pig. Indeed, pet animals, farm animals, experimental animals, and disease-model animals are all contemplated.

A bodily fluid is drawn from a subject and incubated with a divalent cation chelating agent (e.g., EDTA, EGTA, and sodium citrate) or heparin in a container until the sample is separated into an upper layer and a lower layer. From the upper layer, a population of somatic stem cells that are 0.3-6.0 µm in size are isolated and then cultured in a medium containing certain growth factors (i.e., R-Spondin-1, SCF, G-CSF, bFGF, EGF, and PDGF) for 1 to 30 days (e.g., 4 to 14 days). The medium can contain each at a concentration of 1 to 100 ng/ml (e.g., 2 to 50 ng/ml and 5 to 20 ng/ml). Under these culturing conditions, the diameters of the cells increase to 6-25 µm.

The cells that remain non-adherent are SB-3 cells and those that become adherent are SB-4 cells. The somatic stem cells in the SB cell population can be CD9+, SSEA1+, SSEA4+, CD13+, or Stro1+. For example, some are CD9+ CD349+.

Both SB-3 and SB-4 cells are somatic stem cells. They can be used to regenerate differentiated and functional cells for treating various degenerative disorders or tissue damage. These cells can be easily maintained and expanded in vitro, and induced to differentiation using routine technical approaches. In addition, after grafting these stem cells into an animal subject (e.g., a mouse), there is no evidence of malignant growth. These stem cells contain a normal chromosomal complement. They are responsive to lineage-induction agents, proliferation agents, and differentiation inhibitory agents. Due to these advantages, they represent an alternative to other stem cells.

The term "stem cell" herein refers to a cell that is totipotent, pluripotent, multipotent, or unipotent, i.e., capable of differentiating into one or more terminally differentiated cell types. Totipotent stem cells typically have the capacity of developing into any cell type. They can be both embryonic and non-embryonic in origin. Pluripotent cells are typically capable of differentiating into ectoderm, endoderm, and mesoderm cells. Multipotent cells can differentiate into several different, terminally differentiated cell types. Unipotent stem cells can differentiate into only one cell type. They have the property of self-renewal, which distinguishes them from non-stem cells. The above-mentioned stem cells can originate from various tissues or organs, including, but are not limited to, blood, nerve, muscle, skin, gut, bone, kidney, liver, pancreas, and thymus.

The stem cells disclosed herein are substantially pure. The term "substantially pure", when used in reference to stem cells or cells derived therefrom (e.g., differentiated cells), means that the specified cells constitute the majority of cells in the preparation (i.e., more than 20%, 30%, 40%, 50%, 60%, 70%, 80%, 90%, or 95%). Generally, a substantially purified population of cells constitutes at least about 70% of the cells in a preparation, usually about 80% of the cells in a preparation, and particularly at least about 90% of the cells in a preparation (e.g., 95%, 97%, 99% or 100%). As such, a method of the invention provides the advantage that a substantially pure population of a particular type of cells (e.g., SB-3 and SB-4 cells) can be obtained without contamination by other cell types.

Various cell-containing samples from a subject can be used to prepare the somatic stem cells of this invention. In a preferred embodiment of this invention, SB-3 and SB-4 cells are prepared from the SB cell population.

To confirm that the isolated cell is indeed SB-3 or SB-4 cell, one can examine a number of characteristics, including cell surface markers. Antibodies against cell surface markers, such as CD10, CXCR4, CD31, CD105, CD44, and nestin, can be used. They can be conjugated with suitable labels, such as fluorescein isothiocyanate (FITC), phycoerythrin (PE), or quantum dots.

To confirm the differentiation potential of these somatic stem cells, they can be induced to form, for example, neuro-glial cells, osteocytes, and adipocytes by methods known in the art. For example, these cells can be passed and cultured to confluence, shifted to an osteogenic medium or an adipogenic medium, and incubated for a suitable period of time (e.g., 3 weeks). The differentiation potential for osteogenesis is assessed by the mineralization of calcium accumulation, which can be visualized by von Kossa staining. To examine adipogenic differentiation, intracellular lipid droplets can be stained by Oil Red O and observed under a microscope. For neural differentiation, these cells can be incubated in a neurogenic medium for a suitable duration (e.g., 7 days), and then subjected to serum depletion and incubation with β-mercaptoethanol. After differentiation, they exhibit the morphology of refractile cell body with extended neurite-like structures arranged into a network. RT PCR and immunocytochemical stain of lineage specific markers are further conducted to confirm neural differentiation. Examples of the markers include neuron specific class III β-tubulin (Tuj-1), neurofilament, and GFAP.

SB-3 and SB-4 cells can be further propagated in a non-differentiating medium for more than 10, 20, 50, or 100 population doublings without indications of spontaneous differentiation, senescence, morphological changes, increased growth rate, and changes in ability to differentiate into neurons. These stem cells can be stored by standard methods before use.

The terms "proliferation" and "expansion" as used interchangeably herein with reference to cells, refer to an increase in the number of cells of the same type by division. The term "differentiation" refers to a developmental process whereby cells become specialized for a particular function, for example, where cells acquire one or more morphological characteristics and/or functions different from that of the initial cell type. The term "differentiation" includes both lineage commitment and terminal differentiation processes. Differentiation may be assessed, for example, by monitoring the presence or absence of lineage markers, using immunohistochemistry or other procedures known to a worker skilled in the art. Differentiated progeny cells derived from progenitor cells may be, but are not necessarily, related to the same germ layer or tissue as the source tissue of the stem cells. For example, neural progenitor cells and muscle progenitor cells can differentiate into hematopoietic cell lineages.

The terms "lineage commitment" and "specification," as used interchangeably herein, refer to the process a stem cell undergoes in which the stem cell gives rise to a progenitor cell committed to forming a particular limited range of differentiated cell types. Committed progenitor cells are often capable of self-renewal or cell division.

The term "terminal differentiation" refers to the final differentiation of a cell into a mature, fully differentiated cell. For example, neural progenitor cells and muscle progenitor cells can differentiate into hematopoietic cell lineages, terminal differentiation of which leads to mature blood cells of a specific cell type. Usually, terminal differentiation is associated with withdrawal from the cell cycle and cessation of proliferation. The term "progenitor cell," as used herein, refers to a cell that is committed to a particular cell lineage and which gives rise to cells of this lineage by a series of cell divisions. An example of a progenitor cell would be a myoblast, which is capable of differentiation to only one type of cell, but is itself not fully mature or fully differentiated.

Within the scope of this invention is a cell bank or library having a plurality of populations of SB-3 or SB-4 cells. These stem cells can be human cells or non-human cells. The bank can be produced by storing populations of SB-3 or SB-4 cells originated from different subjects; characterizing SB-3 or SB-4 cells in populations to obtain at least one predetermined characteristic for each, and cataloguing each of the populations according to the at least one predetermined characteristic. To produce the bank, one can further expand the populations of SB-3 or SB-4 cells. Examples of the characteristics include a subject's name, gender, physical conditions (including genetic disorders and MHC information)

The above-described SB-3 cells and SB-4 cells can both be used in, among others, drug screening, treating degenerative disorders, and gene therapy.

Screening Methods

The above-described SB-3 cells and SB-4 cells can be used in screening assays to identify drugs that can affect a particular cell type in a manner indicating that the drug can be useful for treating a disorder associated with the cell type. For example, one can use the stem cells in a method for identifying a drug candidate for treating a disease (e.g., a degenerative disease). The method includes the steps of contacting a test compound with the stem cells and determining the expression level of a polypeptide that is down-regulated in the disease. The expression level in the presence of the test compound, if higher than that in the absence of the compound, indicates that the compound is a candidate for treating the disease. Examples of the disease include diabetes, a neurodegenerative disease, arthritis, cancer, or an autoimmune disorder. The expression level can be determined at either the mRNA level or at the protein level.

Thus, one aspect of the present invention relates to a method for identifying an agent that alters a function of SB-3 or SB-4 cells by contacting the cells with a test agent. A change in a function or gene expression of the cells in presence of the test agent as compared to that in the absence of the test agent indicates that the test agent is an agent that alters the function of or the gene expression in the cells. The term "test agent" refers to any molecule that is being examined for an ability to alter a function of or gene expression in the cells. Although the method generally is used as a screening assay to identify previously unknown molecules that have a desired activity, the screening methods of the invention also can be used to confirm a particular activity of an agent known to have the activity.

The function can be expression of a gene that typically is expressed (or not expressed) in the cells, and the agent can alter the function by increasing or decreasing the level of expression of an expressed gene, or by turning on the expression of an unexpressed gene (e.g., inducing expression of lineage-specific antigen) in the cells.

In one embodiment, the agent that affects a function of the cells is one that induces differentiation of stem cells, thereby producing differentiated cells. Such differentiated cells can be multipotential human stem cells (e.g., hematopoietic stem cells) or can be terminally differentiated cells (e.g., muscle cells, liver cells, neuronal cells, blood cells, connective tissue, or epithelial cells). As such, the method can be used to identify an agent that induces differentiation of SB-3 or SB-4 cells to terminally differentiated cells including pancreatic beta cells, hepatocytes, cardiomyocytes, skeletal muscle cells, or any other cell type. Agents or compound thus identified can be used to treat degenerative disorders, cancer, or immune disorders.

The expression level can be determined at either the mRNA level or the protein level. Methods of measuring mRNA levels in a sample are well known in the art. To measure mRNA levels, cells can be lysed and the levels of mRNA in the lysates, whether purified or not, can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out on tissue sections or unlysed cell suspensions using detectably (e.g., fluorescent or enzyme) labeled DNA or RNA probes. Additional mRNA-quantifying methods include the RNAse protection assay (RPA) method and the serial analysis of gene expression (SAGE) method, as well as array-based technologies.

Methods of measuring protein levels in a sample are also well known in the art. Some of them employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin. Its presence can be determined by detectably labeled avidin (a polypeptide that binds to biotin). Combinations of these approaches (including "multi-layer sandwich" assays) can be used to enhance the sensitivity of the methodologies. Appropriate labels include radionuclides (e.g., $^{125}I$, $^{131}I$, $^{35}S$, $^{3}H$, or $^{32}P$), enzymes (e.g., alkaline phosphatase, horseradish peroxidase, luciferase, or β-glactosidase), fluorescent/luminescent agents (e.g., fluorescein, rhodamine, phycoerythrin, GFP, BFP, and nanoparticles (e.g., Qdot™ supplied by the Quantum Dot Corporation, Palo Alto, Calif.). Some protein-measuring assays (e.g., ELISA and Western blot) can be applied to body fluids or to cell lysates, and others (e.g., immunohistological methods and fluorescence flow cytometry) can be applied to histological sections or unlysed cell suspensions. Other applicable methods include quantitative immunoprecipitation and complement fixation assays.

A test compound or agent can be any type of molecule, for example, a polynucleotide, a peptide, a peptidomimetic, peptoids such as vinylogous peptides, a small organic molecule, or the like, and can act in any of various ways to alter a function of SB-3 or SB-4 cells. For example, the test agent can act extracellularly by binding to a cell surface receptor expressed by the cells, thereby altering a function mediated by binding of a ligand that generally binds to and acts via the receptor. Alternatively, the test agent can be one that traverses the cell membrane, either passively or via an active transport mechanism, and acts within the cells to alter a function.

A peptide test agent can be any polymer of amino acids or amino acid analogs, and can vary from about three to four residues to hundreds or thousands. Peptide test agents can be prepared by chemical synthesis, or using methods of protein purification, followed by proteolysis and, if desired, further purification by chromatographic or electrophoretic methods, or can be expressed from an encoding polynucleotide. A peptide test agent can be based on a known peptide, for example, a naturally occurring peptide, but can vary from the naturally occurring sequence, for example, by containing one or more amino acid analogs.

A polynucleotide agent can be a sequence of two or more deoxyribonucleotides or ribonucleotides that are linked together by a phosphodiester bond. It can be RNA or DNA, which can be a gene or a portion thereof, a cDNA, an RNAi agent, a synthetic polydeoxy-ribonucleic acid sequence, or the like, and can be single stranded or double stranded, as well as a DNA/RNA hybrid. It can be a naturally occurring nucleic acid molecule, which can be isolated from a cell, as well as a synthetic molecule, which can be prepared, for example, by methods of chemical synthesis or by enzymatic methods such as by the polymerase chain reaction (PCR). In various embodiments, a polynucleotide of the invention can contain nucleoside or nucleotide analogs, or a backbone bond other than a phosphodiester bond. Such nucleotide analogs are well known in the art and commercially available, as are polynucleotides containing such nucleotide analogs (Pagratis et al., Nature Biotechnol. 15:68-73, 1997).

A polynucleotide test agent can be contacted with or introduced into SB-3 or SB-4 cells using methods as disclosed herein or otherwise known in the art. Generally, but not necessarily, the polynucleotide is introduced into the cell, where it effects its function either directly, or following transcription or translation or both. For example, the polynucleotide can encode a peptide test agent, which is expressed in the cells and alters a function of the cells. A polynucleotide test agent also can be, or can encode, an antisense molecule, a ribozyme or a triplexing agent, which can be designed to target one or more specific target nucleic acid molecules.

Candidate agents or compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Lam, 1997, Anticancer Drug Des. 12:145. Examples of methods for the synthesis of molecular libraries can be found in, e.g., Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Felici 1991, J. Mol. Biol. 222:301-310; and U.S. Pat. No. 5,223,409).

Treatment Methods

One can use SB-3 or SB-4 cells disclosed herein for treating degenerative or inherited diseases, avoiding ethical considerations of human embryo manipulation.

To do so, one can isolate a SB cell population from a patient, e.g., a patient lacking a functional gene essential for proper development of a tissue or organ. The SB cell population is subsequently subjected to conditions so as to obtain SB-3 cells or SB-4 cells. One can then introduce into these stem cells an expression nucleic acid vector encoding a functional version of the gene. The vector can be introduced into the stem cells via a variety of techniques, including calcium phosphate co-precipitation, DEAE-dextran-mediated transfection, lipofection, electroporation, microinjection, or virus-meditated techniques. Methods not affecting the pluripotency of the cells are preferred. Description of such techniques can be found in publications, e.g., U.S. Pat. Nos. 7,422,736 and 5,591,625. After delivering the functional gene into the stem cells, one can transplant them back into the patient using method known in the art. As the stem cells are produced from the patient, the treatment does not cause immune rejection.

Alternatively, one can make universal donor cells from SB-3 or SB-4 cells prepared from a healthy subject. Methods for making universal donor cells are known in the art. Exemplary techniques for making universal pluripotent stem cells from SB-3 or SB-4 cells are described below.

Under proper conditions, the transplanted stem cells can develop into a functional tissue or organ. To facilitate this development, the patient may be administered with factors to induce the development of the cells. Such factors can be small molecule compounds, peptides, and nucleic acids. Examples include, but are not limited to, transforming growth factor β, bone morphogenic proteins, and nerve growth factor.

The universal pluripotent stem cells are also useful for studying development or differentiation mechanisms of lineage development and differentiation. One can identify conditions for inducing the development of totipoent pluripotent stem cells into a specific tissue or organ using such cells as a model system. Further, one can isolate genes that play roles during the development using differential cDNA screening known in the art. One can prepare a cDNA library from the cells that have been induced to develop into a certain lineage, e.g., neuro-glial lineage described above. The library can then be used to isolate and study genes differentially expressed. These isolated genes can be further studied to define their roles in respective processes. The related techniques are known in the art. See e.g., U.S. Pat. No. 7,422,736. The pluripotent stem cells can also be used to develop into organs or clones of the animals using the methods known in the art. Accordingly, these cells are valuable for the pet and livestock industries, and can be used to preserve endangered animals.

In one aspect, the invention features a method of treating a degenerative disease in a subject. The method includes administering to a subject in need thereof an effective amount of the above-described SB-3 or SB-4 cells. In one embodiment, at least one of these cells includes a recombinant nucleic acid. The recombinant nucleic acid can encode a polypeptide and the stem cell can contain an mRNA encoding the polypeptide. Examples of the degenerative disease include a muscle degenerative disease, a liver degenerative disease, diabetes, a neurodegenerative disease, and arthritis. An example of a neurodegenerative disease is Parkinson's disease.

In another aspect, the invention features a method of treating an autoimmune disease in a subject. The method includes administering to a subject in need thereof an effective amount of the above-described SB-3 or SB-4 cells.

A degenerative disease refers to a disorder where the function or structure of an affected tissue or organ progressively deteriorate over time, whether due to genetic defects, injury, lack of proper cell differentiation (e.g., that in cell proliferative disorders), normal bodily wear, or lifestyle choices. Examples of degenerative diseases include neurodegenerative diseases (e.g., Alzheimer's disease, Parkinson's disease, Huntington's disease, multiple sclerosis, and amyotrophic lateral sclerosis (ALS)); other nervous system disorders (e.g., transverse myelitis, demyelination occurring after trauma to the brain or spinal cord, acute brain injury, head trauma, spinal cord injury, peripheral nerve injury, ischaemic brain injury, hereditary myelin disorder of the CNS, epilepsy, perinatal asphxia, asphyxia, anoxia, status epilepticus, Shy-Drager syndrome, autism, and stroke); cancer (e.g., liver cancer) or a condition resulting from anticancer therapy (e.g., chemotherapy); metabolic disorders (e.g., diabetes/diabetes mellitus and Niemann Pick disease); autoimmune or inflammation related disorders (e.g., erythematosis, inflammatory bowel disease (IBD), prostatitis, osteoarthritis, osteoporosis, rheumatoid arthritis, lupus, diabetes, and asthma); ocular disorders (e.g., glaucoma, retinitis pigmentosa, Norrie disease, and macular degeneration); heart and circulatory disorders (e.g., atherosclerosis, heart failure myocardial infarction, and cardiovascular disease); blood disorders (e.g., Wiscott Aldrich syndrome); muscular dystrophy; gastrointestinal disease; kidney disease; liver disease; lung disease; adrenal disorders (e.g., Addison's disease); a condition resulting from an injury (e.g., a burn, a stroke, damaged tissue including flesh wounds, age damaged cells, and age damaged tissue); a condition associated with aging (e.g., hair loss, including male pattern baldness and alopecia areata); viral conditions (e.g., hepatitis C infection and acquired immune deficiency disorder); and any other disorder that an organ transplant or stem cells can be used to restore, regenerate, or otherwise ameliorate signs and/or symptoms associated with the disorder. The method of this invention can be used in treating erectile dysfunction and in plastic surgery or breast implantation for female.

In yet another aspect, described herein a method of treating brain or CNS tissue damage or alleviating the symptom of the disorder in a subject. The method includes identifying a subject suffering from or being at risk for developing brain tissue damage. Examples of the brain tissue damage include those caused by a cerebral ischemia (e.g., chronic stroke) or a neurodegenerative disease (e.g., Parkinson's disease, Alzheimer's disease, Spinocerebellar disease, and Huntington's disease). The treatment method entails administering to a subject in need thereof an effective amount of the above-described stem cells or active agents/compounds.

The therapeutic effects of the stem cells can be accessed according to standard methods. For example, to confirm efficacy in promoting cerebrovascular angiogenesis, one can examine the subject before and after the treatment by standard brain imaging techniques, such as computed tomography (CT), Doppler ultrasound imaging (DUI), magnetic resonance imaging (MRI), and proton magnetic resonance spectroscopy ($^1$H-MRS). For example, $^1$H-MRS represents a non-invasive means to obtain biochemical information correlated to brain metabolic activity (Lu et al., 1997, Magn. Reson. Med. 37, 18-23). This technique can be applied to evaluate the metabolic changes involved in cerebral ischemia with or without stem cell transplantation. For example, it can be used to study the N-acetylaspartate (NAA) concentration in the brain, a marker of neuronal integrity. Although NAA redistribution and trapping in neuronal debris limits its use as a quantitative neuronal marker, decreases in brain NAA concentration in cerebral ischemia can be considered as an index of neuronal loss or dysfunction (Demougeot et al., 2004, J. Neurochem. 90, 776-83). Therefore, an NAA level, measured by $^1$H-MRS, is a useful indicator for following the effect of stem cell transplantation after cerebral ischemia.

A subject to be treated for one of the above-described disorders can be identified by standard diagnosing techniques for that particular disorder. "Treating" refers to administration of a composition (e.g., a cell composition) to a subject, who is suffering from or is at risk for developing that disorder, with the purpose to cure, alleviate, relieve, remedy, delay the onset of, prevent, or ameliorate the disorder, the symptom of the disorder, the disease state secondary to the disorder, or the predisposition toward the damage/disorder. A subject to be treated can be identified by standard techniques for diagnosing the conditions or disorders of interest. An "effective amount" refers to an amount of the composition that is capable of producing a medically desirable result in a treated subject. The treatment method can be performed alone or in conjunction with other drugs or therapies. The subject can be a human or a non-human mammal, such as a cat, a dog, or a horse.

Making and Using Liver Cells

Also within the scope of this invention are methods of making and using liver cells derived from SB-4 cells. SB-4 cells undergo differentiation to form endoderm cells when cultured in a medium containing activin for five days, then in a medium containing bFGF and BMP2 for ten to fifteen days, finally in a medium containing HGF, DEX, and OSM for ten to fifteen days. These endoderm cells express albumin, transferrin, and HNF3B, all of which are liver-specific proteins. In other words, SB-4 cells can differentiate into liver cells for use in producing albumin or for use in a bioartificial liver device. Herein, the term "liver cells" is interchangeable with the word "hepatocytes." One embodiment of this invention is an extracorporeal bioartificial liver device that uses the liver cells derived from SB-4 cells. Such a device is used to treat a subject having or suspected of having a liver-related condition or compromised liver function resulting either from disease or trauma.

Figure 2:
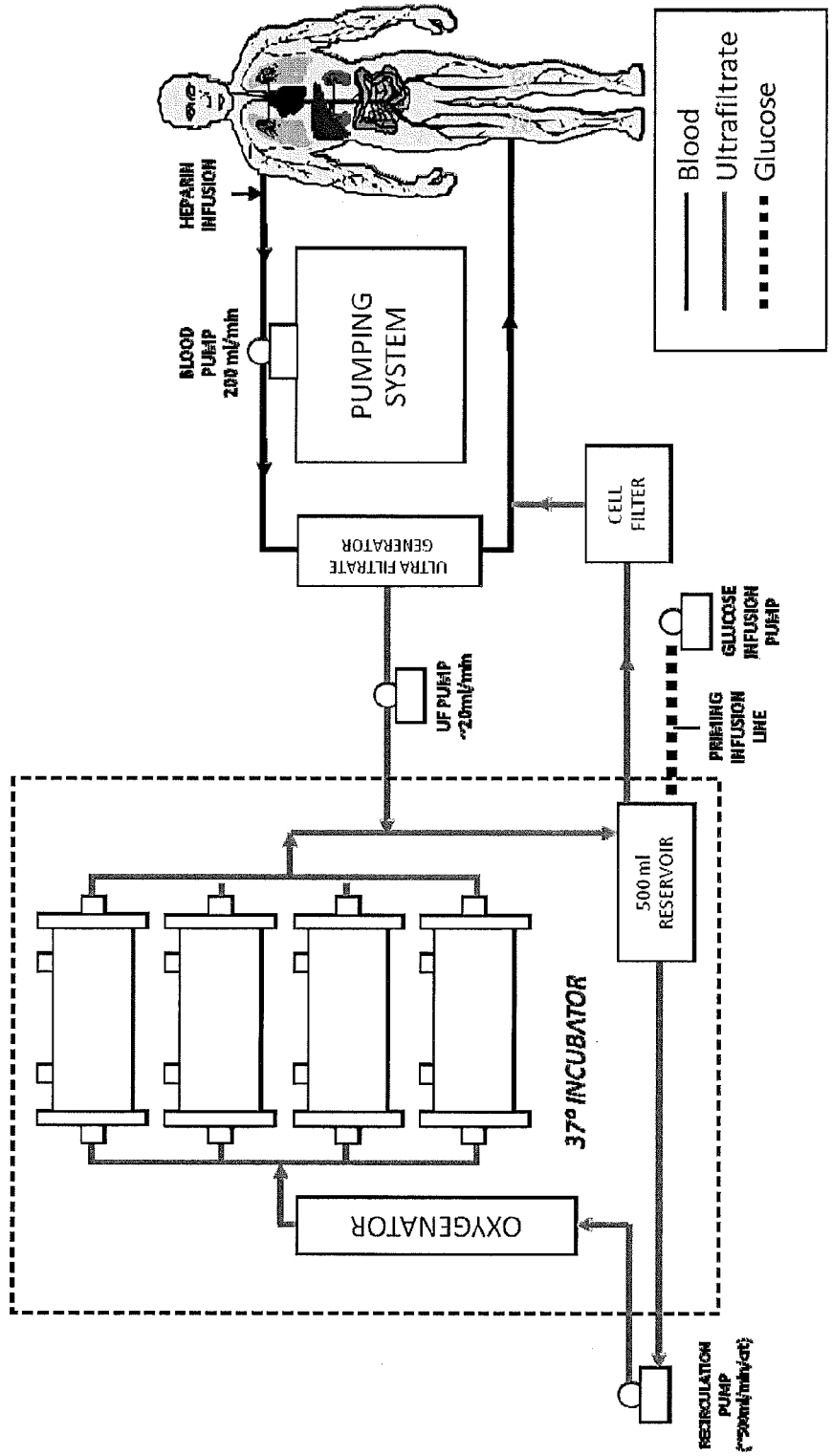
FIG. 2 is a schematic presentation of an extracorporeal bioartificial liver device that is attached to a human subject.
Figure 3A:
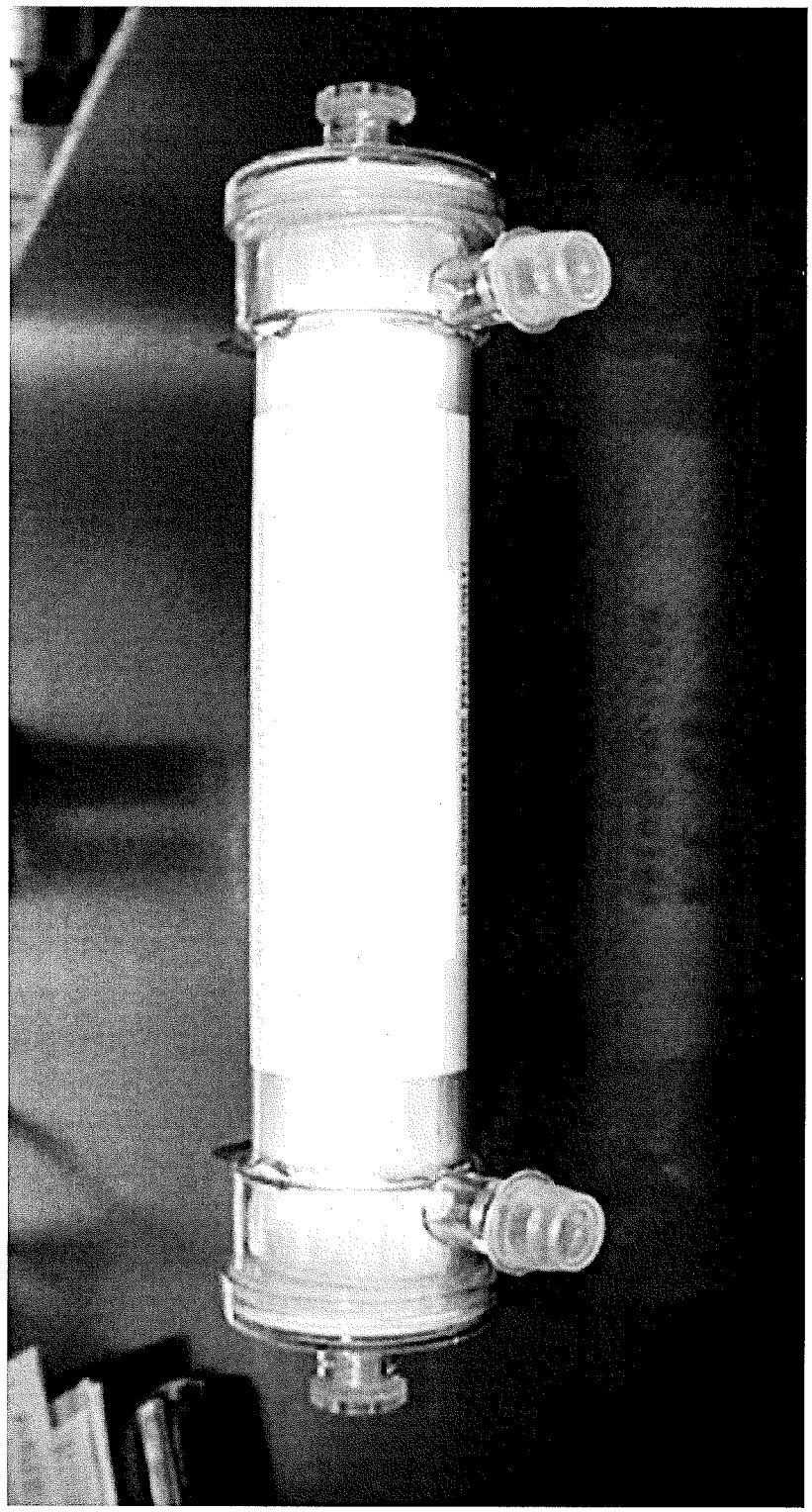
FIG. 3a is a photograph of an exemplary cartridge that can be used in an extracorporeal bioartificial liver device.
Figure 3B:
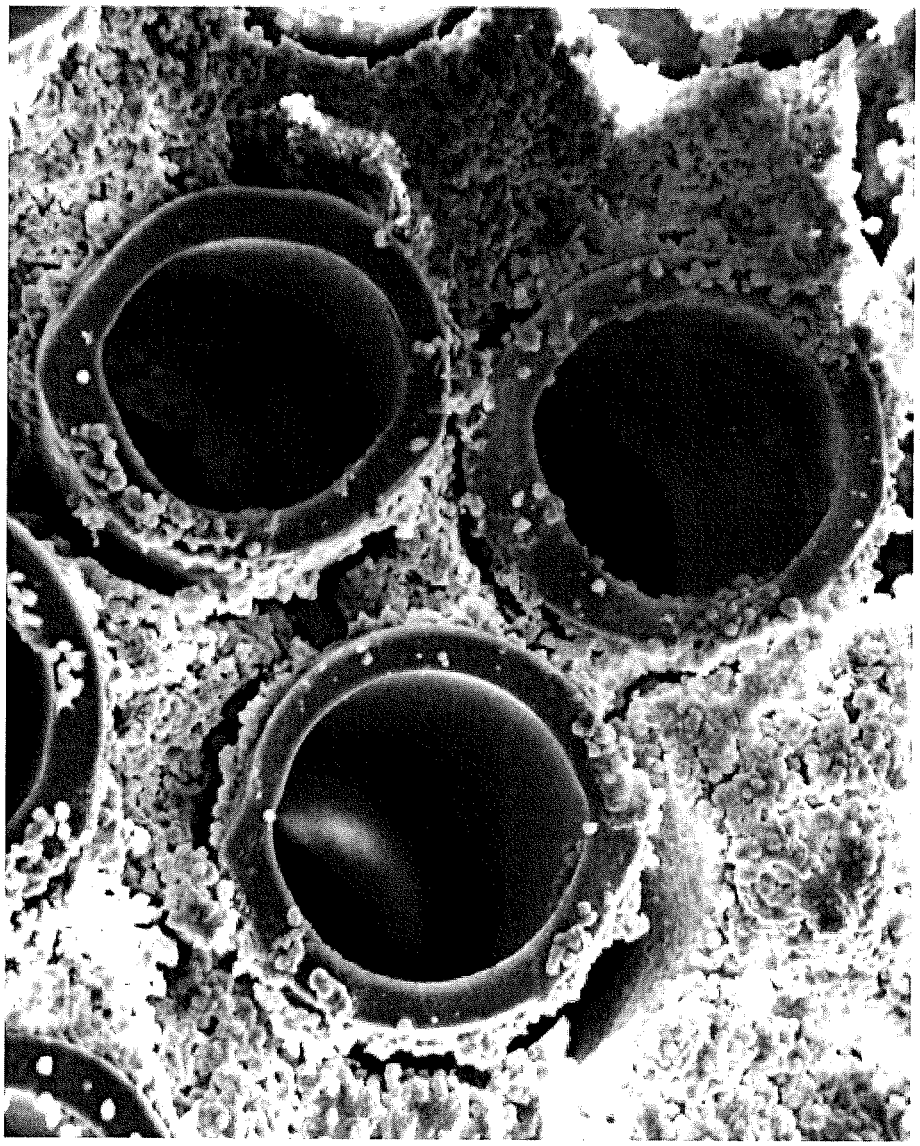
FIG. 3b is an image of a cross-section of the exemplary cartridge.

The extracorporeal bioartificial liver device includes one or more cartridges. See FIG. 2. Each cartridge contains an array of hollow fibers each formed of a permeable or semi-permeable membrane. See FIGS. 3a and 3b. Each cartridge can have a cylindrical shape with a first opening at one terminus and a second opening at the other terminus; and the first opening is affixed to a first passage and the second opening is affixed to a second passage, the two passages extending away from the cartridge. See FIG. 3a. One passage is attached to an artery of a subject and the other to a vein of this subject.

The membrane forming each hollow fiber allows cleansing of blood by permitting crossover of toxic solutes from the blood to the liver cells cultured inside the hollow fibers (e.g., bilirubin, which diffuses through the membrane and are taken up and metabolized) and also by permitting diffusion of vital metabolites from cells cultured in the device to the blood returning to the subject. The selectively permeable or semi-permeable character of the membrane also provides a mechanical barrier to components of the immune system in the blood of the subject. Typically, the membrane features a molecular weight cutoff from about 20,000 daltons up to about 80,000 daltons, generally about 30,000 daltons to about 50,000 daltons. In a preferred embodiment, the membrane has pores of 0.1 µm to 0.3 µm in diameter, typically about 0.2 µm. A pore diameter in this range, while excluding cellular elements, permits proteins (e.g., albumin) and protein complexes to pass through, thus ameliorating serum protein deficiencies of a subject suffering from liver failure.

The term "cleanse" or "clean," as used herein, means removal of unwanted or undesired molecules from the subject's blood. Moreover, the term "cleanse" or "clean" further includes release of desired molecules (i.e., albumin) from the SB-4-derived liver cells into the blood before returning it to the subject.

Similar devices, their use, and mechanisms of action are commonly known to a person of ordinary skill in the art. For example, bio-artificial liver devices are described in Viles, et al., U.S. Pat. Nos. 4,675,002 and 4,853,324; Jauregin, GB 2,221,857A; Wolf et al., 1979, International J. of Artificial Organs 2:97-103; Wolf et al., 1978, International J. of Artificial Organs, 1:45-51; and Ehrlich et al., 1978, In Vitro 14:443-450. Such devices are also contemplated to be used with the SB-4 cells-derived liver cells.

Hollow fiber cartridges have two-chamber units, i.e., one chamber located inside each of the hollow fibers and the other located outside the hollow fibers, which reproduce the three-dimensional characteristics of normal organs. See Knazek, R. H., 1974, Feder. Proc. 33:1978-1981; and Ku, K. et al., 1983, Biotechnol. Bioeng. 23:79-95.

Culture or growth medium is circulated through the capillary space inside each of the hollow fibers in the cartridge and the cells, grown in the extracapillary space between the hollow fibers in the cartridge after seeding, are supplied with a constant inflow of fresh medium. See Tharakan, J. P. et al., 1986, Biotechnol. Bioeng. 28:1605-1611. Typically, 1400 $cm^2$ cartridges are inoculated with an effective number of SB-4 cell-derived liver cells (e.g., approximately, $1 \times 10^9$ cells) and grown to confluence in 14 to about 21 days. Such hollow fiber culture systems are well known (e.g., Heifetz et al., 1989, BioTechniques 7:192-199; and Donofrio, D., Amer. Biotech. Lab. September 1989, Publication #940) and available commercially (e.g., the Anchornet series).

Hollow fiber-based systems when used in a bio-artificial liver device offer several advantages. Cartridges support the growth of very high-density cultures. Based on the extracapillary volume, 15 to 20 g of cells are grown in a 1400 $cm^2$ unit and 100 g of cells are grown in a 7000 $cm^2$. This amount of cell mass is capable of providing liver support to a subject suffering from liver failure. Also, cartridge-grown cells are polarized and their growth approximates normal liver structure. The cells receive nutrients from the capillary space and secrete waste products into the extracapillary space. The extracapillary space is perfused to prevent the accumulation of toxic products. The continual flow of media and the in-line oxygenator provide a more constant supply of oxygen and energy.

For the most part, the bio-artificial liver devices contemplated to be used with the SB-4-derived liver cells primarily process blood by extracorporeally attaching to a subject (e.g., typically, making fluid communication from the device to the subject's blood supply usually between an artery and a vein). Such an arrangement is particularly useful for providing temporary liver support for subjects suffering from a severe liver disorder.

Alternatively, the SB-4-derived liver cells are used within the body as a bio-artificial liver or as a bio-artificial liver support. When used in this manner, the SB-4-derived liver cells are encapsulated or grown in hollow fiber capillary membranes for internal use. Typically, the cells attach to the support upon growth. Linkage materials, however, may be provided to attach the cells to a support (see, e.g., Jauregin, GB 2,221,857A). The SB-4-derived liver cells are encapsulated in biomaterial such as alginate-polylysine membranes, as taught by Cai et al., Artificial Organs 12:388-393; Sun et al., 1986, Trans. Am. Soc. Artif. Intern. Organs Vol. XXXII: 39-41; O'Shea et al., 1984, Biochimica Biophysica Acta 804:133-136; Sun et al., 1985, J. Controlled Release 2:137-141; and Lim, U.S. Pat. No. 4,391,909. The encapsulated cells and vehicle capsules are then injected intra-peritoneally into the subject.

Additionally, the SB-4-derived liver cells can be used in a synthetic liver-like tissue comprising fibroblasts and the SB-4-derived liver cells. Typically, co-culture of fibroblasts and hepatocytes do not automatically adopt the arrangement typically found in the liver. Further, as the two cell types communicate poorly, the hepatocytes are often functionally inefficient. To solve this problem, one can imprint a substrate (e.g., a borosilicate wafer) using standard photolithographic techniques of microelectronic technology with patterned films of collagen, which promotes cell adhesion. See Toner et al., 1997, Fall Meeting of the Materials Research Association, 1-5; Toner et al., 1988, Nature, 39: 128. The SB-4-derived liver cells can then be cultured on such surfaces, adhering only to the collagen-coated regions. Fibroblasts are subsequently introduced onto the bare surface regions producing an intimate mixture of the two cell types in a periodic pattern. This technique allows any ratio of cell types on the substrate and thus permits adjustment to any physiological value. Further, any pattern size, shape, and number density can be deduced and engineered.

Gene Therapy

The stem cells described herein can be used to express an exogenous, recombinant polypeptide. Thus, within the scope of this invention are such stem cells, which contain a recombinant nucleic acid. The recombinant nucleic acid can encode a polypeptide and the stem cells can contain an mRNA encoding the polypeptide.

These stem cells can be genetically manipulated so that they do not express the beta2-microglobulin gene or do not express one or more proteins encoded by the class I major histocompatibility complex (MHC) genes that elicit a T lymphocyte mediated reaction against the cell. These cells can be used as universal donor cells since they do not lead to host rejections of grafts.

Accordingly, the invention features a method for introducing a heterologous nucleic acid in a subject. The method includes the steps of obtaining the above-described stem cells, where at least one of the stem cells includes a heterologous nucleic acid, and administering the cell into a subject in need thereof. The heterologous nucleic acid can encode a polypeptide.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell. Similarly, a heterologous protein indicates that the protein comprises two or more subsequences that are not found in the same relationship to each other in nature (e.g., a "fusion protein," where the two subsequences are encoded by a single nucleic acid sequence). Such protein can be generated by recombinant techniques. The term "recombinant" when used with reference, e.g., to a cell, nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

The above-described stem cells and methods can be used in various gene therapy methods known in the art. Gene therapy includes both ex vivo and in vivo techniques. Specifically, the above-described stem cells can be genetically engineered ex vivo with an oligonucleotide modulator or a nucleic acid molecule encoding the modulator, with the engineered cells then being provided to a patient to be treated. Cell cultures may be formulated for administration to a patient, for example, by dissociating the cells (e.g., by mechanical dissociation) and intimately admixing the cell with a pharmaceutically acceptable carrier (e.g., phosphate buffered saline solution). Alternatively, cells may be cultured on a suitable biocompatible support and transplanted into a patient. The engineered cells are typically autologous so as to circumvent xenogeneic or allotypic rejection. Such ex vivo methods are well known in the art.

The cells can be engineered by administration of the oligonucleotide or nucleic acid molecule using techniques known in the art. For example, oligonucleotides and other nucleic acid molecules can be administered by direct injection of a "naked" nucleic acid molecule (U.S. Pat. No. 5,679,647) or a nucleic acid molecule formulated in a composition with one or more other agents which facilitate uptake of the nucleic acid molecule by the cell, such as saponins (see, for example, U.S. Pat. No. 5,739,118) or cationic polyamines (see, for example, U.S. Pat. No. 5,837,533); by microparticle bombardment (for example, through use of a "gene gun"; Biolistic, Dupont); by coating the nucleic acid molecule with lipids, cell-surface receptors or transfecting agents; by encapsulation of the nucleic acid molecule in liposomes, microparticles, or microcapsules; by administration of the nucleic acid molecule linked to a peptide which is known to enter the nucleus; or by administration of the nucleic acid molecule linked to a ligand subject to receptor-mediated endocytosis, which can be used to target cell types specifically expressing the receptors.

A nucleic acid-ligand complex can be formed in which the ligand comprises a fusogenic viral peptide to disrupt endosomes, allowing the nucleic acid to avoid lysosomal degradation; or the nucleic acid molecule can be targeted for cell specific uptake and expression in vivo by targeting a specific receptor. In addition, an efficient method for the introduction, expression and accumulation of antisense oligonucleotides in the cell nucleus is described in U.S. Pat. No. 6,265,167, which allows the antisense oligonucleotide to hybridise to the sense mRNA in the nucleus, and thereby prevents the antisense oligonucleotide being either processed or transported into the cytoplasm. The present invention also contemplates the intracellular introduction of the nucleic acid molecule and subsequent incorporation within host cell DNA for expression by homologous recombination known in the art.

The polynucleotide can also be incorporated into a suitable expression vector. A number of vectors suitable for gene therapy applications are known in the art (see, for example, Viral Vectors: Basic Science and Gene Therapy, Eaton Publishing Co. (2000)).

The expression vector may be a plasmid vector. Methods of generating and purifying plasmid DNA are rapid and straightforward. In addition, plasmid DNA typically does not integrate into the genome of the host cell, but is maintained in an episomal location as a discrete entity eliminating genotoxicity issues that chromosomal integration may raise. A variety of plasmids are now readily available commercially and include those derived from *Escherichia coli* and *Bacillus subtilis*, with many being designed particularly for use in mammalian systems. Examples of plasmids that may be used in the present invention include, but are not limited to, the eukaryotic expression vectors pRc/CMV (Invitrogen), pCR2.1 (Invitrogen), pAd/CMV and pAd/TR5/GFPq (Massie et al., (1998) Cytotechnology 28:53-64). In an exemplary embodiment, the plasmid is pRc/CMV, pRc/CMV2 (Invitrogen), pAdCMV5 (IRB-NRC), pcDNA3 (Invitrogen), pAdMLP5 (IRB-NRC), or PVAX Invitrogen).

The expression vector can be a viral-based vector. Examples of viral-based vectors include, but are not limited to, those derived from replication deficient retrovirus, lentivirus, adenovirus and adeno-associated virus. Retrovirus vectors and adeno-associated virus vectors are currently the recombinant gene delivery system of choice for the transfer of exogenous oligonucleotides or genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. Retroviruses, from which retroviral vectors may be derived include, but are not limited to, Moloney Murine Leukemia Virus, spleen necrosis virus, Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. Specific retroviruses include pLJ, pZIP, pWE and pEM, which are well known to those skilled in the art.

Cell Banking

The invention features a stem cell bank or library for a convenient systematic access to different stem cell lines. SB-3 or SB-4 cells in the bank or library are derived from a healthy subject or subject having known disease state or disease symptom would be invaluable to users, e.g., researchers. Also with the scope of the invention is a cell bank or library having cells differentiated from the above-described stem cells. Examples of cells differentiated from the stem cells include brain cells, neurons, astrocytes, glial cells, T cells, B cells, cartilage cells, bone cells, pancreatic islet cells, fat cells, heart cells, liver cells, kidney cells, lung cells, muscle cells, and eye cells. The subjects may be human or nonhuman vertebrates. The stem cells can be derived from any mammalian organism, such as human, mouse, rabbits, cows, pigs, and the like.

The cells in the bank or library are catalogued according to predetermined characteristics, including phenotypic information, morphological characteristics, differentiation profile, blood type, major histocompatibility complex, disease state of donor, or genotypic information (e.g. single nucleated polymorphisms (SNPs) of a specific nucleic acid sequence associated with a gene, or genomic or mitochondrial DNA). The cells are stored under appropriate conditions (typically by freezing) to keep the stem cells alive and functioning. Cataloguing may constitute creating a centralized record of the characteristics obtained for each cell population, such as, but not limited to, an assembled written record or a computer database with information inputted therein. Essentially, this embodiment pertains to the production of a stem cell bank. The stem cell bank facilitates the selection from a plurality of samples of a specific stem cell sample suitable for a user's needs. Thus, another embodiment of the subject invention pertains to a stem cell bank comprising a plurality of stem cells samples obtained from separate sources and which are characterized and catalogued according to at least one predetermined characteristic. An additional embodiment pertains to a method of establishing a stem cell bank comprising collecting stem samples from multiple sources; cataloguing the samples according to at least one predetermined characteristic and storing the cells under conditions that keep cells viable.

With the scope of this invention is a stem cell banking system containing a plurality of stem cell populations disposed in individual containers under conditions to keep the stem cell populations viable; a database computer comprising at least one processing module, a display, and a storage medium comprising information of at least one characteristic for each stem cell population; and at least one program code module for causing the information to be viewable on said display upon command by a user. In a specific embodiment, the invention features a stem cell banking system where stem cell populations have stem cells obtained from subjects who have a disease condition. The disease condition may include the above-described degenerative diseases. SB-3 or SB-4 cells derived from different subjects having different diseases, and the stem cells are characterized. The characteristic(s) is/are inputted into the database computer. In addition, or alternatively, cells are characterized based on a specific phenotype not necessarily associated with a disease condition. For example, liver cells can be characterized based on their ability to metabolize certain compounds such as caffeine, alcohol, drug agents, etc. to study genetic bases of such different metabolism abilities, or underlying physiology associated therewith. Other types of cells can be characterized based on functional and/or morphological phenotypes.

In certain embodiments, cells differentiated from SB-3 or SB-4 cells may be subjected to conditions to influence differentiation or dedifferentiation through introduction of engineered vectors, or other genetic material. Dedifferentiation comprises the manipulation of a cell such that it takes on the properties of a less differentiated cell.

The stem cell libraries of the invention can be used to screen for agents or compounds that may be used to treat degenerative disorders, cancer or immune disorders in the manner described above. The libraries are suitable for high throughput screening and are useful for identifying agents that are specifically effective for a particular subject. For a high throughput screening, stem cells can be introduced into wells of a multiwell plate or of a glass slide or microchip, and can be contacted with the test agent. Generally, the cells are organized in an array, particularly an addressable array, such that robotics conveniently can be used for manipulating the cells and solutions and for monitoring the cells, particularly with respect to the function being examined. An advantage of using a high throughput format is that a number of test agents can be examined in parallel, and, if desired, control reactions also can be run under identical conditions as the test conditions. As such, the screening methods of the invention provide a means to screen one, a few, or a large number of test agents in order to identify an agent that can alter a function of stem cells, for example, an agent that induces the cells to differentiate into a desired cell type, or that prevents spontaneous differentiation, for example, by maintaining a high level of expression of regulatory molecules.

Universal Donor Cells

The above-described stem cells can be genetically engineered to generate histocompatible donor cells or tissues for transplantation. The goal of transplantation and cell therapy is to successfully replace failing tissues or organs with functional donor tissues or organs. However, for transplantation to succeed, two major barriers need to be overcome: the availability of suitable donor tissues or organs and immune rejection. The replacement of failing tissues or organs and the treatment of the rejection is restricted by the limited number of acceptable donors and the need for co-administration of toxic immuno-suppressive drugs in conjunction with long term immuno-suppressive protocols. Current and experimental transplantation protocols rely mainly on sibling donors, other small pools of allogeneic donors, and xenogeneic donors. The above-described genetically engineered stem cells can be used to overcome these limitations.

More specifically, the stem cells described herein can be genetically engineered to not express on their surface class II MHC molecules. More preferably, the cells are engineered to not express substantially all cell surface class I and class II MHC molecules. As used herein, the term "not express" means either that an insufficient amount is expressed on the surface of the cell to elicit a response or that the protein that is expressed is deficient and therefore does not elicit a response.

The MHC molecules refer to HLA molecules, specifically of classes HLA A, B and C, and class II HLA DP, DQ, and DR, and their subclasses. This terminology is generally construed as specific to the human MHC, but is intended herein to include the equivalent MHC genes from the donor cell species, for example, if the cells are of porcine origin, the term HLA would refer to the equivalent porcine MHC molecules, whether MHC I or II. When the class II MHC molecules are removed, CD4+ T-cells do not recognize the genetically engineered endothelial cells; when both the class I and class II MHC molecules are removed neither CD4+ nor CD8+ cells recognize the modified cells.

The preferred genetic modification performed on the stem cells includes 1) disrupting the endogenous invariant chain gene which functions in the assembly and transport of class II MHC molecules to the cell surface and loading of antigenic peptide, and 2) disrupting the endogenous $\beta_2$-microglobulin gene ($\beta_2$M gene), which codes for a protein required for the cell surface expression of all class I MHC molecules. Alternatively, just the invariant chain gene is disrupted. Invariant chain is believed to be required for the insertion of antigenic peptide fragments into the MHC class II molecule. Together, the antigenic peptide and MHC are recognized by T cells. In the absence of antigenic peptide, T cell recognition is not normally obtained, nor is the MHC class II molecule folded properly. Thus, in cells lacking invariant chain, presentation of peptide will be abrogated and even if minuscule amounts of cell surface MHC are obtained, they may be devoid of peptide and therefore, non-immunogenic.

Disruption of these genes can be accomplished by means of homologous recombination gene targeting techniques. These techniques are well known in the art. See, e.g., U.S. Pat. Nos. 6,916,654 and 6,986,887.

Compositions

The present invention provides for pharmaceutical compositions containing the SB-3 or SB-4 cells or active agents/compounds. Pharmaceutical compositions can be prepared by mixing a therapeutically effective amount of the cells or active agents/compounds, and, optionally other active substance, with a pharmaceutically acceptable carrier. The carrier can have different forms, depending on the route of administration. Examples of other active substance include active compounds known or identified by the screening method of described above.

The above-described pharmaceutical compositions can be prepared by using conventional pharmaceutical excipients and methods of preparation. All excipients may be mixed with disintegrating agents, solvents, granulating agents, moisturizers, and binders. As used herein, the term "effective amount" or 'therapeutically effective amount' refers to an amount which results in measurable amelioration of at least one symptom or parameter of a specific disorder. A therapeutically effective amount of the above-described stem cells can be determined by methods known in the art. An effective amount for treating a disorder can easily be determined by empirical methods known to those of ordinary skill in the art. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of the above-described disorders is within the scope of the invention. Clinically significant attenuation or amelioration means perceptible to the patient and/or to the physician.

The phrase "pharmaceutically acceptable" refers to molecular entities and other ingredients of such compositions that are physiologically tolerable and do not typically produce unwanted reactions when administered to a human. Preferably, the term "pharmaceutically acceptable" means approved by a regulatory agency of the federal or a state government or listed in the U.S. Pharmacopeia or other generally recognized pharmacopeia for use in mammals, and more particularly in humans. Pharmaceutically acceptable salts, esters, amides, and prodrugs refers to those salts (e.g., carboxylate salts, amino acid addition salts), esters, amides, and prodrugs which are, within the scope of sound medical judgment, suitable for use in contact with the tissues of patients without undue toxicity, irritation, allergic response, and the like, commensurate with a reasonable benefit/risk ratio, and effective for their intended use.

A carrier applied to the pharmaceutical compositions described above refers to a diluent, excipient, or vehicle with which a compound is administered. Such pharmaceutical carriers can be sterile liquids, such as water and oils. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th edition.

The above-described stem cells can be administered to individuals through infusion or injection (for example, intravenous, intrathecal, intramuscular, intraluminal, intratracheal, intraperitoneal, or subcutaneous), orally, transdermally, or other methods known in the art. Administration may be once every two weeks, once a week, or more often, but frequency may be decreased during a maintenance phase of the disease or disorder.

Both heterologous and autologous cells can be used. In the former case, HLA-matching should be conducted to avoid or minimize host reactions. In the latter case, autologous cells are enriched and purified from a subject and stored for later use. The cells may be cultured in the presence of host or graft T cells ex vivo and re-introduced into the host. This may have the advantage of the host recognizing the cells as self and better providing reduction in T cell activity.

The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the above-described composition. Dosages and administration regimen can be adjusted depending on the age, sex, physical condition of administered as well as the benefit of the conjugate and side effects in the patient or mammalian subject to be treated and the judgment of the physician, as is appreciated by those skilled in the art. In all of the above-described methods, the stem cells can be administered to a subject at $1 \times 10^4$ to $1 \times 10^{10}$/time.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Example 1

A blood sample or a bone marrow sample was drawn from a person and placed in an anti-clotting EDTA tube or heparin tube. After allowing the tube to rest for 72 hours at 4° C., the sample separated into two layers. The bottom layer, which appeared red, consisted almost entirely of red (RBC) and white blood cells. The top layer contained cells having diameters of less than 6 μm, named SB cells. SB cells are described in further detail in US2012/0034194.

SB cells were then cultured in a StemPro-34 medium (INVITROGEN) containing 5 ng/ml R-Spondin-1, 5 ng/ml SCF, 5 ng/ml G-CSF, 20 ng/ml bFGF, 20 ng/ml EGF, and 5 ng/ml PDGF for 4 to 14 days. Under the above-mentioned culturing condition, the diameters of the cells increased to 6-25 μm. The cells that remained non-adherent were named SB-3 cells, and those that became adherent were named SB-4 cells. SB-4 cells are round or oval, and larger in size, i.e., 7-30 μm, than SB-3 cells.

CD349 antibody was used to isolate CD349+ cells from the SB mixture. Also see US2012/0034194. These CD349+ cells cultured in the same way as SB cells also grew into SB-3 cells and attach to the walls as SB-4 cells.

Tests showed that SB-3 cells have the ability to expand. SB-4 cells were able to undergo proliferation and differentiation as long as the desired growth factor was added. SB-4 cells were able to undergo at least 40 passages with normal karyotype and normal telomerase activity. Cultured SB-4 cells had a doubling time around 24 hours.

RT-PCR analyses show that SB-3 cells expressed CD10, CXCR4, and CD31, but not CD9, CD349, CD271, CD133, CD66e, CD45, CD20, or CD4. SB-4 cells expressed CD105, CD44, and nestin, but not CD34, CD90, CD41, CD117, α-fetoprotein, POU5F1, Nanog, Sox2, HNF4a, CD36, HNF3B, Pax6, or Pax7. The primers for RT-PCR are shown in Table 1 below:

TABLE 1

| Gene | Primer |
|---|---|
| α-fetoprotein | F: 5'-AAATGCGTTTCTCGTTGCTT-3' (SEQ ID NO: 1)<br>R: 5'-GCCACAGGCCAATAGTTTGT-3' (SEQ ID NO: 2) |
| B-actin | F: 5'-AGCCTCGCCTTTGCCGA-3' (SEQ ID NO: 3)<br>R: 5'-CTGGTGCCTGGGGCG-3' (SEQ ID NO: 4) |
| CD10 | F: 5'-GGT TGG GAG CTG ATG AAA CT-3' (SEQ ID NO: 5)<br>R: 5'-GAA TAG GGC TGG AAC AAG GA-3' (SEQ ID NO: 6) |
| CD105 | F: 5'-CAC TAG CCA GGT CTC GAA GG-3' (SEQ ID NO: 7)<br>R: 5'-CTG AGG ACC AGA AGC ACC TC-3' (SEQ ID NO: 8) |
| CD117 | F: 5'-TAAGTCAGATGCGGCCATGACTGT 3' (SEQ ID NO: 9)<br>R: 5'-TGGTGCAGGCTCCAAGTAGATTCA-3' SEQ ID NO: 10) |
| CD133 | F: 5'-AGC GAT CAA GGA GAC CAA AG-3' (SEQ ID NO: 11)<br>R: 5'-AAG CAC AGA GGG TCA TTG AG-3' (SEQ ID NO: 12) |
| CD271 | F: 5'-CCG CAA AGC GGA CCG AGC TG-3' (SEQ ID NO: 13)<br>R: 5'-CGT CAC GCT GTC CAG GCA GG-3' (SEQ ID NO: 14) |
| CD31 | F: 5'-CACAACAGACATGGCAACAAGGCT-3' (SEQ ID NO: 15)<br>R: 5'-TCCTTCTGGATGGTGAAGTTGGCT-3' (SEQ ID NO: 16) |
| CD34 | F: 5'-CCT TGA ACC ACT TCC CTC AT-3' (SEQ ID NO: 17)<br>R: 5'-TAG GCT CCA GCC AGA AAA CT-3' (SEQ ID NO: 18) |
| CD349 | F: 5'-TCT TCC ACA TCC GCA AGA TCA-3' (SEQ ID NO: 19)<br>R: 5'-AGT CCA TGT TGA GGC GTT CGT A-3' (SEQ ID NO: 20) |
| CD36 | F: 5-CAGGAGTTTGCAAGAAACAGGTGC-3' (SEQ ID NO: 21)<br>R: 5'-ATACCTCCAAACACAGCCAGGACA-3' (SEQ ID NO: 22) |

TABLE 1-continued

| Gene | Primer |
|---|---|
| CD4 | F: 5'-GTA GTA GCC CCT CAG TGC AA-3' (SEQ ID NO: 23)<br>R: 5'-AAA GCT AGC ACC ACG ATG TC-3' (SEQ ID NO: 24) |
| CD41 | F: 5'-AAT GGC CCC TGC TGT CGT GC-3' (SEQ ID NO: 25)<br>R: 5'-TGC ACG GCC AGC TCT GCT TC-3' (SEQ ID NO: 26) |
| CD44 | F: 5'-TCGAAGAAGGTGTGGGCAGAAGA-3' (SEQ ID NO: 27)<br>R: 5'-ATTTCCTGAGACTTGCTGGCCTCT-3' (SEQ ID NO: 28) |
| CD66e | F: 5'-TAT ACG TGC CAA GCC CAT AA-3' (SEQ ID NO: 29)<br>R: 5'-TAC AGC ATC CTC ATC CTC CA-3' (SEQ ID NO: 30) |
| CD9 | F: 5'-TGC GTT GAA CTG CTG TGG TTT G-3' (SEQ ID NO: 31)<br>R: 5'-GCG CCG ATG ATG TGG AAT TT-3' (SEQ ID NO: 32) |
| CD90 | F: 5'-CATAACGCTCTCACCCTCTC-3' (SEQ ID NO: 33)<br>R: 5'-CTCTTCACCCCATTCACACC-3' (SEQ ID NO: 34) |
| CXCR4 | F: 5'-GTT GGC TGA AAA GGT GGT CT-3' (SEQ ID NO: 35)<br>R: 5'-CAC AAC CAC CCA CAA GTC AT-3' (SEQ ID NO: 36) |
| GAPDH | F: 5'-GAG TCA ACG GAT TTG GTC GT-3' (SEQ ID NO: 37)<br>R: 5'-TTG ATT TTG GAG GGA TCT CG-3' (SEQ ID NO: 38) |
| HNF3B | F: 5'-CCATGCACTCGGCTTCCAGTATG-3' (SEQ ID NO: 39)<br>R: 5'-CGCCGACATGCTCATGTACGTG-3' (SEQ ID NO: 40) |
| HNF4a | F: 5'-TGTGAGTGGCCCCGACCCTG-3' (SEQ ID NO: 41)<br>R: 5'-ACGATTGTGGCGACGGCTCC-3' (SEQ ID NO: 42) |
| CD20 set 1 | F: 5'-GCT GCC ATT TCT GGA ATG AT-3' (SEQ ID NO: 43)<br>R: 5'-TTC CTG GAA GAA GGC AAA GA-3' (SEQ ID NO: 44) |
| CD20 set 2 | F: 5'-GTT TTT GGT GGA GTC CCT TT-3' (SEQ ID NO: 45)<br>R: 5'-AAA CAG ATG GGT GTT GGC TA-3' (SEQ ID NO: 46) |
| Nanog | F: 5'-TGT GAT TTG TGG GCC TGA AGA-3' (SEQ ID NO: 47)<br>R: 5'-TTG TTT GCC TTT GGG ACT GG-3' (SEQ ID NO: 48) |
| Nestin | F: 5'-TGCCCGGCACTGGGGACTTA-3' (SEQ ID NO: 49)<br>R: 5'-TAGCGGGCCAGGCCTCTCAG-3' (SEQ ID NO: 50) |
| Pax 7 | F: 5'-CGA CTC CGG ATG TAG AGA AA-3' (SEQ ID NO: 51)<br>R: 5'-TTC CCG AAC TTG ATT CTG AG-3' (SEQ ID NO: 52) |
| Pax6 | F: 5'-AGT GGG TTT GAA AAG GGA AC-3' (SEQ ID NO: 53)<br>R: 5'-ATT GGT GAT GGC TCA AGT GT-3' (SEQ ID NO: 54) |

TABLE 1-continued

| | |
|---|---|
| POU5F1 | F: 5'-GGA CCA GTG TCC TTT CCT CT-3' (SEQ ID NO: 55)<br>R: 5'-CCA GGT TTT CTT TCC CTA GC-3' (SEQ ID NO: 56) |
| CD45 | F: 5'-CCT GCT CAG AAT GGA CAA GT-3' (SEQ ID NO: 57)<br>R: 5'-TCA GAA CCT TCA GCC TGT TC-3' (SEQ ID NO: 58) |
| Sox2 | F: 5'-GAA ATG GGA GGG GTG CAA AA-3' (SEQ ID NO: 59)<br>R: 5'-ATC GCG GTT TTT GCG TGA GT-3' (SEQ ID NO: 60) |

Example 2

Assays were carried out to demonstrate that SB-3 are stem cells capable of differentiating into different cells lineages.

Briefly, SB-3 cells were obtained from a subject in the manner described above. SB-3 cells were then cultured in a differentiation medium. All primers used for detecting differentiation markers with real time RT-PCR are listed in Table 2 below.

SB-3 cells were induced to express nestin, an early marker for formation of neuron (ectoderm) and islet cells (endoderm). Briefly, SB-3 cells were cultured in an induction medium that contains 10 nM glucocorticoid and 10% FBS. After 1-month treatment, RNA was extracted and gene expression was determined by Real Time PCR. Expression of nestin was detected.

TABLE 2

| | |
|---|---|
| GABAR | F: 5'-TTATCTCACCCCTTCCTTGG-3' (SEQ ID NO: 61)<br>R: 5'-GCCATCATGTAGCATTCCTG-3' (SEQ ID NO: 62) |
| Albumin | F: 5'-TGTGAAACACAAGCCCAAGGCA-3' (SEQ ID NO: 63)<br>R: 5'-CCCTCCTCGGCAAAGCAGGT-3' (SEQ ID NO: 64) |
| CD31 | F: 5'-CAGGCTTCGGCTCAGGCACC-3' (SEQ ID NO: 65)<br>R: 5'-ATCGGGGCCGGGTGACTTCA-3' (SEQ ID NO: 66) |
| NR4A2 | F: 5'-GCTCAAGGAACCCAAGAGAG-3' (SEQ ID NO: 67)<br>R: 5'-GGCACCAAGTCTTCCAATTT-3' (SEQ ID NO: 68) |
| MAP-2 | F: 5'-CGCACACCAGGCACTCCTGG-3' (SEQ ID NO: 69)<br>R: 5'-CACCTGGCCTGTGGCGGATG-3' (SEQ ID NO: 70) |
| N-Cam | F: 5'-CTCCAGCACAGCCCAGGTGC-3' (SEQ ID NO: 71)<br>R: 5'-TGCTGGCTTCCTTGGCATCATGC-3' (SEQ ID NO: 72) |
| Tau | F: 5'-AAGATCGGCTCCACTGAGAA-3' (SEQ ID NO: 73)<br>R: 5'-GGACGTGGGTGATATTGTCC-3' (SEQ ID NO: 74) |
| Insulin | F: 5'-AGCCTTTGTGAACCACACC-3' (SEQ ID NO: 75)<br>R: 5'-GCTGGTAGAGGGAGCAGATG-3' (SEQ ID NO: 76) |

TABLE 2-continued

| | |
|---|---|
| Transferrin | F: 5'-GAGGCCACTAAGTGCCAGAG-3' (SEQ ID NO: 77)<br>R: 5'-TTCTTCACCACAGCAACAGC-3' (SEQ ID NO: 78) |
| Tyrosine Hydroxylase | F: 5'-GCTCAGGAGCTATGCCTCAC-3' (SEQ ID NO: 79)<br>R: 5'-ACCTAGCCAATGGCACTCAG-3' (SEQ ID NO: 80) |
| Neurofilament-M | F: 5'-AAGTCAGACCAAGCCGAAGA-3' (SEQ ID NO: 81)<br>R: 5'-GCACAGGAGACTTGCCTTTC-3' (SEQ ID NO: 82) |
| Myosin heavy chain alpha 6 (cardiomyocyte) | F: 5'-GCTGGAGTCCTCACAGAAGG-3' (SEQ ID NO: 83)<br>R: 5'-TCTCCAGCTCATGCACATTC-3' (SEQ ID NO: 84) |
| Myosin light chain 1 fast (skeletal myocyte) | F: 5'-TTCAGTGCTGACCAGATTGC-3' (SEQ ID NO: 85)<br>R: 5'-AAATGGCTTGCATCATAGGC-3' (SEQ ID NO: 86) |
| Osteocalcin (OC) | F: 5'-TGAGAGCCCTCACACTCCTC-3' (SEQ ID NO: 87)<br>R: 5'-TCAGCCAACTCGTCACAGTC-3' (SEQ ID NO: 88) |
| a-fetoprotein | F: 5'-AAATGCGTTTCTCGTTGCTT-3' (SEQ ID NO: 1)<br>R: 5'-GCCACAGGCCAATAGTTTGT-3' (SEQ ID NO: 2) |
| HNF4a | F: 5'-TGTGAGTGGCCCCGACCCTG-3' (SEQ ID NO: 41)<br>R: 5'-ACGATTGTGGCGACGGCTCC-3' (SEQ ID NO: 42) |
| CD133 | F: 5'-AGC GAT CAA GGA GAC CAA AG-3' (SEQ ID NO: 11)<br>R: 5'-AAG CAC AGA GGG TCA TTG AG-3' (SEQ ID NO: 12) |
| CD44 | F: 5'-TCGAAGAAGGTGTGGGCAGAAGA-3' (SEQ ID NO: 27)<br>R: 5'-ATTTCCTGAGACTTGCTGGCCTCT-3' (SEQ ID NO: 28) |
| CD10 | F: 5'-GGT TGG GAG CTG ATG AAA CT-3' (SEQ ID NO: 5)<br>R: 5'-GAA TAG GGC TGG AAC AAG GA-3' (SEQ ID NO: 6) |
| CXCR4 | F: 5'-GTT GGC TGA AAA GGT GGT CT-3' (SEQ ID NO: 35)<br>R: 5'-CAC AAC CAC CCA CAA GTC AT-3' (SEQ ID NO: 36) |
| Nestin | F: 5'-TGCCCGGCACTGGGGACTTA-3' (SEQ ID NO: 49)<br>R: 5'-TAGCGGGCCAGGCCTCTCAG-3' (SEQ ID NO: 50) |
| CD105 | F: 5'-CAC TAG CCA GGT CTC GAA GG-3' (SEQ ID NO: 7)<br>R: 5'-CTG AGG ACC AGA AGC ACC TC-3' (SEQ ID NO: 8) |

Endoderm cells are characterized by their polygonal shapes. Expression of two hepatocyte markers (transferrin and albumin) and three islet cell markers (insulin, alpha-Fetoprotein, and HNF4 alpha) were detected. In addition, both Western blot and ELISA also detected expression of albumin in differentiated cells. These results indicate that SB-3 cells were differentiated into hepatocytes and some were differentiated into islet cells.

Ectoderm cells are characterized by their filament-like feature. Differentiation of SB-3 cells to neuronal cells were confirmed by real time RT-PCR, which detected expression of many neuronal markers, including CD133, nestin, microtubule-associate protein II, GABA receptor, NR4A2, N-cam, tyrosine hydroxylase, neurofilament, and Tau.

Further, SB-3 cells were induced to differentiate into adipocytes or osteogenic cells, i.e., mesoderm cells. SB-3 cells were cultured in media A, B, C, D, and E sequentially. Then, the medium was replaced by an adipocyte differentiation medium (Invitrogen) for 8 weeks. The adipocytes were stained using Oil-red-0 and detected in an OD490 ELISA spectrophotometer. Alternatively, the medium was replaced by an osteogenesis medium (Invitrogen). Osteogenic cells were observed 2-4 weeks after the medium replacement. Osteogenic cells were stained with Alizarin Red, and detected by extracting from the cells Alizarin Red, which was measured at OD 405 nm in a spectrophotometer. The results show that SB-3 cells can be differentiated to adipocytes or osteogenic cells.

For induction to other mesoderm cells, SB-3 cells were cultured in the medium that contained 10 nM glucocorticoid and 10% FBS. After 1-month treatment, RNA was extracted from the cells, and expression of several genes was determined by Real Time PCR. Detectable expression of myosin heavy chain and skeletal myosin light chain indicates SB-3 cells were differentiated to cardiomyocyte and skeletal muscle cells.

The above results suggest that, upon receipt of a signal, SB-3 cells are activated and differentiate into suitable tissues to repair the damaged tissues. Thus, these cells contain adult pluripotent stem cells and can be used for gene therapy, gene banking, drug screening, and creating universal donor cells. Also, these cells could be used to treat degenerative diseases, autoimmune diseases, or cancer.

Example 3

SB-4 cells were cultured in four different types of media and analyzed to confirm that differentiation was successful. To test mesoderm differentiation, cells were cultured in adipogenesis and osteogenesis media. Oil-Red O and Alizarin Red staining indicated significant increases in adipocytes and osteocytes, respectively, when compared to their negative controls.

To investigate ectoderm differentiation ability, SB-4 cells were cultured in neuron differentiation medium. Results from ICC neurofilament staining and real time-PCR confirmed that SB-4 has neuron differentiation ability.

SB-4 cells were also induced to differentiate to hepatocytes by culturing them successively in three different media as follows.

First, SB-4 cells were cultured for five days in a DMEM/high glucose medium containing 3% horse serum, 1× antimycotic, 1×L-glutamine, and 5 ng/mL activin. Next, the cells were further cultured for fifteen days in the same medium except that activin was replaced with 20 ng/mL bFGF and 5 ng/mL BMP2. Finally, the cells were cultured in a Hepato ZYME-SFM medium containing 1% horse serum, 10 ng/mL HGF, 10 nM glucocorticoid DEX, and 10 ng/mL OSM for fifteen days or until hepatocyte-like cells appear. The culturing medium was routinely refreshed at least twice a week. The hepatocyte-like cells were observed by microscope. Further, they were tested for expression of heptocyte markers by real time RT-PCR with the primers listed in Table 3 below:

TABLE 3

| Albumin | F: 5'-GAAACATTCACCTTCCATGC-3' (SEQ ID NO: 89) R: 5'-ACAAAAGCTGCGAAATCATC-3' (SEQ ID NO: 90) |
|---|---|
| Transferrin | F: 5'-GGAGCCTTCAAGTGTCTGAA-3' (SEQ ID NO: 91) R: 5'-GTTGAGAAGCTCCCAGATCA-3' (SEQ ID NO: 92) |
| HNF 3B | F: 5'-CCATGCACTCGGCTTCCAGTATG-3' (SEQ ID NO: 93) R: 5'-CGCCGACATGCTCATGTACGTG-3' (SEQ ID NO: 94) |

The results show that the hepatocyte-like cells indeed expressed three heptocyte markers, i.e., albumin, transferrin, and HNF-3beta.

We believe that these hepatocyte-like cells can have the ability to metabolize and successfully remove toxins, such as ammonia, and synthesize urea for the detoxification. Thus, the hepatocyte-like cells can be used as the artificial liver system which is able to replicate human liver functions and support patients with acute liver failure. In addition, our hepatocyte-like cells can produce albumin which is an important product for marketing since it can be used as a carrier for small pill/drug.

Thus, these hepatocyte-like cells can be used to make artificial liver system and facilitate drug delivery. These cells would also be useful for treating liver degenerative disease and liver cancer.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. A method of preparing somatic stem cells, the method comprising:
   incubating a bodily fluid sample containing a plurality of cells with EDTA or heparin in a container until the sample is separated into an upper layer and a lower layer,
   collecting the upper layer,
   isolating from the upper layer a population of somatic stem cells that are 0.3-6.0 micrometers in size, and
   culturing the isolated somatic stem cells in a medium containing R-Spondin-1, SCF, G-CSF, bFGF, EGF, and PDGF.

2. The method of claim 1, wherein the somatic stem cells are CD10+, CXCR4+, and CD31+.

3. The method of claim 1, wherein the somatic stem cells are CD105+, CD44+, and Nestin+.

4. The method of claim 1, wherein the bodily fluid sample is a blood sample or a bone marrow sample.

5. A method of preparing liver cells from somatic stem cells, the method comprising:
   culturing the isolated somatic stem cells prepared by the method of claim 1 in a first differentiating medium containing activin;
   culturing the isolated somatic stem cell in a second differentiating medium containing basic FGF and BMP2;
   culturing the isolated somatic stem cell in a third differentiating medium containing HGF, and DEX, and OSM; and
   collecting liver cells thus obtained, the liver cells expressing albumin, transferrin, and HNF3B.

6. A method of producing albumin, comprising:
   culturing in a medium the liver cells prepared by the method of claim 5, and
   collecting from the medium albumin produced by the liver cells.

7. A method of preparing islet cells, neuronal cells, adipocytes, or osteogenic cells from somatic stem cells, the method comprising: culturing the isolated somatic stem cells prepared by the method of claim 1 in a differentiation medium under conditions that allow the isolated somatic stem cells to differentiate into hepatocytes, islet cells, neuronal cells, adipocytes, or osteogenic cells.

* * * * *

SEQUENCE LISTING

<160> NUMBER OF SEQ ID NOS: 92

<210> SEQ ID NO 1
<211> LENGTH: 20
<212> TYPE: DNA
<213> ORGANISM: Artificial sequence -continued

```
<220> FEATURE:
<223> OTHER INFORMATION: Synthetic oligonucleotide

<400> SEQUENCE: 1
aaatgcgttt ctcgttgctt                                                    20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
gccacaggcc aatagtttgt                                                    20

<210> SEQ ID NO 3
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 3
agcctcgcct ttgccga                                                       17

<210> SEQ ID NO 4
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 4
ctggtgcctg gggcg                                                         15

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
ggttgggagc tgatgaaact                                                    20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
gaatagggct ggaacaagga                                                    20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
cactagccag gtctcgaagg                                                    20
```

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ctgaggacca gaagcacctc                                               20

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
taagtcagat gcggccatga ctgt                                          24

<210> SEQ ID NO 10
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 10
tggtgcaggc tccaagtaga ttca                                          24

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
agcgatcaag gagaccaaag                                               20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
aagcacagag ggtcattgag                                               20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
ccgcaaagcg gaccgagctg                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 14
cgtcacgctg tccaggcagg                                            20

<210> SEQ ID NO 15
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 15
cacaacagac atggcaacaa ggct                                       24

<210> SEQ ID NO 16
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 16
tccttctgga tggtgaagtt ggct                                       24

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ccttgaacca cttccctcat                                            20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
taggctccag ccagaaaact                                            20

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
tcttccacat ccgcaagatc a                                          21

<210> SEQ ID NO 20
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 20
agtccatgtt gaggcgttcg ta                                         22

<210> SEQ ID NO 21
```

```
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 21
caggagtttg caagaaacag gtgc                                              24

<210> SEQ ID NO 22
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 22
atacctccaa acacagccag gaca                                              24

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
gtagtagccc ctcagtgcaa                                                   20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
aaagctagca ccacgatgtc                                                   20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
aatggcccct gctgtcgtgc                                                   20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tgcacggcca gctctgcttc                                                   20

<210> SEQ ID NO 27
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 27
```
tcgaagaagg tgtgggcaga aga                                               23

<210> SEQ ID NO 28
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 28
atttcctgag acttgctggc ctct                                              24

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
tatacgtgcc aagcccataa                                                   20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
tacagcatcc tcatcctcca                                                   20

<210> SEQ ID NO 31
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 31
tgcgttgaac tgctgtggtt tg                                                22

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
gcgccgatga tgtggaattt                                                   20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
cataacgctc tcaccctctc                                                   20

<210> SEQ ID NO 34
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 34
ctcttcaccc cattcacacc                                                     20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
gttggctgaa aaggtggtct                                                     20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
cacaaccacc cacaagtcat                                                     20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gagtcaacgg atttggtcgt                                                     20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ttgattttgg agggatctcg                                                     20

<210> SEQ ID NO 39
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 39
ccatgcactc ggcttccagt atg                                                 23

<210> SEQ ID NO 40
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 40
cgccgacatg ctcatgtacg tg                                                  22
```

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tgtgagtggc cccgaccctg                                                  20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
acgattgtgg cgacggctcc                                                  20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
gctgccattt ctggaatgat                                                  20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ttcctggaag aaggcaaaga                                                  20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
gtttttggtg gagtcccttt                                                  20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
aaacagatgg gtgttggcta                                                  20

<210> SEQ ID NO 47
<211> LENGTH: 21
<212> TYPE: DNA
<213> ORGANISM: Artificial sequence
<220> FEATURE:

<223> OTHER INFORMATION: Synthetic oligonucleotide

<400> SEQUENCE: 47
tgtgatttgt gggcctgaag a                                          21

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
ttgtttgcct ttgggactgg                                            20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
tgcccggcac tgggactta                                             20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
tagcgggcca ggcctctcag                                            20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
cgactccgga tgtagagaaa                                            20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
ttcccgaact tgattctgag                                            20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
agtgggtttg aaaagggaac                                            20

```
<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
attggtgatg gctcaagtgt                                               20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
ggaccagtgt cctttcctct                                               20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
ccaggttttc tttccctagc                                               20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
cctgctcaga atggacaagt                                               20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
tcagaacctt cagcctgttc                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
gaaatgggag gggtgcaaaa                                               20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide
```

-continued

```
<400> SEQUENCE: 60
atcgcggttt ttgcgtgagt                                               20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
ttatctcacc ccttccttgg                                               20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
gccatcatgt agcattcctg                                               20

<210> SEQ ID NO 63
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 63
tgtgaaacac aagcccaagg ca                                            22

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
ccctcctcgg caaagcaggt                                               20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
caggcttcgg ctcaggcacc                                               20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
atcggggccg ggtgacttca                                               20

<210> SEQ ID NO 67
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 67
gctcaaggaa cccaagagag                                              20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
ggcaccaagt cttccaattt                                              20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
cgcacaccag gcactcctgg                                              20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
cacctggcct gtggcggatg                                              20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
ctccagcaca gcccaggtgc                                              20

<210> SEQ ID NO 72
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 72
tgctggcttc cttggcatca tgc                                          23

<210> SEQ ID NO 73
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 73
aagatcggct ccactgagaa                                              20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
ggacgtgggt gatattgtcc                                              20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
agcctttgtg aaccaacacc                                              20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
gctggtagag ggagcagatg                                              20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
gaggccacta agtgccagag                                              20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
ttcttcacca cagcaacagc                                              20

<210> SEQ ID NO 79
<211> LENGTH: 20
<212> TYPE: DNA
<213> ORGANISM: Artificial sequence
```

-continued

<220> FEATURE:
<223> OTHER INFORMATION: Synthetic oligonucleotide

<400> SEQUENCE: 79
gctcaggagc tatgcctcac                                                    20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
acctagccaa tggcactcag                                                    20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
aagtcagacc aagccgaaga                                                    20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
gcacaggaga cttgcctttc                                                    20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
gctggagtcc tcacagaagg                                                    20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
tctccagctc atgcacattc                                                    20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
ttcagtgctg accagattgc                                              20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
aaatggcttg catcataggc                                              20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
tgagagccct cacactcctc                                              20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
tcagccaact cgtcacagtc                                              20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
gaaacattca ccttccatgc                                              20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
acaaaagctg cgaaatcatc                                              20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
ggagccttca agtgtctgaa                                              20

```
<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
gttgagaagc tcccagatca                                              20
```